United States Patent [19]

Schneider et al.

[11] Patent Number: 4,904,300
[45] Date of Patent: Feb. 27, 1990

[54] IMIDAZOLE DERIVATIVES

[75] Inventors: Hans-Dieter Schneider, Weil am Rhein, Fed. Rep. of Germany; William R. Lutz, Riehen; Henry Szczepanski, Wallbach, both of Switzerland; Werner Töpfl, Dornach, Switzerland

[73] Assignee: Ciba-Geigy Corp., Ardsley, N.Y.

[21] Appl. No.: 233,299

[22] Filed: Aug. 17, 1988

[30] Foreign Application Priority Data

Aug. 26, 1987 [CH] Switzerland .................. 03262/87

[51] Int. Cl.$^4$ .................. A01N 43/50; C07D 405/04
[52] U.S. Cl. .................................. 71/92; 71/90; 71/91; 544/6; 544/58.6; 544/70; 544/96; 544/230; 544/333; 546/141; 546/144; 548/146; 548/147; 548/215; 548/216; 548/336
[58] Field of Search .................. 548/336; 71/90, 91, 71/92

[56] References Cited

U.S. PATENT DOCUMENTS 3,485,917  12/1969  Godefrol et al. .................. 424/273
3,873,297  3/1975   Kupelian .................. 71/78
4,813,998  3/1989   Van Lommen et al. .................. 548/336

FOREIGN PATENT DOCUMENTS 207563  7/1987  European Pat. Off. .

Primary Examiner—Glennon H. Hollrah
Assistant Examiner—James H. Turnipseed
Attorney, Agent, or Firm—Kevin T. Mansfield; Edward M. Roberts

[57] ABSTRACT

Imidazole derivatives of formula I

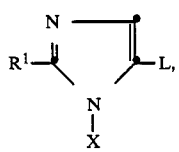

and the stereochemically isomeric forms thereof, and salts thereof, have useful herbicidal properties. The substituents $R^1$, L and X have the meanings defined herein.

20 Claims, No Drawings

IMIDAZOLE DERIVATIVES

The present invention relates to novel herbicidally active isochromanimidazole, isothiochromanimidazole and tetrahydroisoquinolineimidazole derivatives, to agrochemical compositions containing these compounds, and to a method for controlling weeds, preferably for selectively controlling weeds in crops of useful plants. The invention relates also to a process for the preparation of the novel compounds, and to novel intermediates.

The invention relates to herbicidally active isochroman-, isothiochroman- and tetrahydroisoquinoline-imidazole derivatives corresponding to the formula I

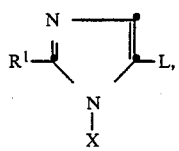

the stereochemically isomeric forms thereof, and salts thereof, in which
X is a radical of the formula

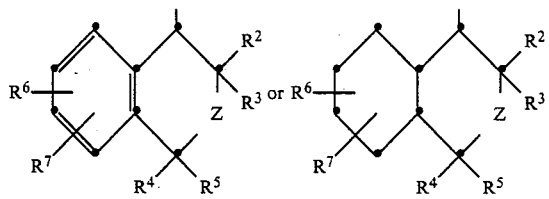

$R^1$ is hydrogen or —SH, and
L is cyano, —COOH, —COOR$^8$, —COSR$^8$, —CONR$^9$R$^{10}$, —CO—R$^{11}$, —CH$_2$—O—R$^{12}$ or a group

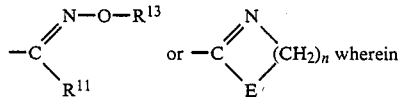 wherein

E is oxygen, sulfur, —N(C$_1$–C$_4$alkyl)- or —NH—,
n is 2 or 3,
Z is oxygen, sulfur, —SO—, —SO$_2$— or —NR$^{14}$—,
each of R$^2$ and R$^3$, independently of the other, is hydrogen, C$_1$–C$_4$alkyl, C$_2$–C$_4$alkenyl or C$_2$–C$_4$alkynyl or together they form a spirocyclically linked C$_2$–C$_6$alkylene chain,
each of R$^4$ and R$^5$, independently of the other, is hydrogen or C$_1$–C$_4$alkyl or together they form an oxo function,
R$^6$ is hydrogen, cyano, halogen, C$_1$–C$_4$alkyl, C$_1$–C$_4$haloalkyl, C$_1$–C$_4$alkoxy, C$_1$–C$_4$haloalkoxy, C$_1$–C$_4$alkylthio, C$_1$–C$_4$haloalkylthio or nitro,
R$^7$ is hydrogen, C$_1$–C$_4$alkoxy, halogen, or C$_1$–C$_4$alkyl,
R$^8$ is C$_1$–C$_6$alkyl, C$_3$–C$_7$cycloalkyl, C$_2$–C$_6$alkoxyalkyl, benzyl, —CR$^{15}$R$^{16}$—C$_2$–C$_4$alkenyl or —CR$^{15}$R$^{16}$—C$_2$–C$_6$alkynyl,
R$^9$ is hydrogen, C$_1$–C$_4$alkyl, C$_1$–C$_4$alkoxy, phenyl, benzyl, —CR$^{15}$R$^{16}$—C$_2$–C$_4$alkenyl or —CR$^{15}$R$^{16}$—C$_2$–C$_4$alkynyl,
R$^{10}$ is hydrogen or C$_1$–C$_4$alkyl, or R$^9$ and R$^{10}$ together with the nitrogen atom carrying them form a pyrrolidine, piperidine or morpholine radical,
R$^{11}$ is C$_1$–C$_6$alkyl, C$_3$–C$_7$cycloalkyl, C$_1$–C$_4$haloalkyl, or phenyl that is unsubstituted or substituted by C$_1$–C$_4$alkyl, C$_1$–C$_4$alkoxy, nitro or by halogen,
R$^{12}$ is hydrogen, C$_1$–C$_6$alkyl, phenyl that is unsubstituted or substituted by C$_1$–C$_4$alkyl, C$_1$–C$_4$alkoxy, halogen or by nitro, C$_1$–C$_6$alkylcarbonyl, C$_1$–C$_4$haloalkylcarbonyl, or benzoyl that is unsubstituted or substituted by C$_1$–C$_4$alkyl, C$_1$–C$_4$alkoxy, halogen or by nitro,
R$^{13}$ is C$_1$–C$_4$alkyl, —CR$^{15}$R$^{16}$—C$_2$–C$_4$alkenyl, benzyl or —CR$^{15}$R$^{16}$—C$_2$–C$_4$-chloroalkenyl,
R$^{14}$ is hydrogen, C$_1$–C$_4$alkyl, C$_1$–C$_4$alkylcarbonyl, C$_1$–C$_4$alkoxycarbonyl, benzyloxycarbonyl, benzoyl or benzyl, and
each R$^{15}$ and R$^{16}$, independently of the other, is hydrogen or C$_1$–C$_4$-alkyl.

5-imidazolecarboxylic acid derivatives having tetralinyl and indanyl substituents in position 1 are known, together with their biological activity and methods of preparation, from European patent application No. EP-A-207 563.

Surprisingly, the compounds of formula I have strong herbicidal properties which allow the control of weeds. The importance of this property is increased by the fact that some useful plant crops are not damaged by treatment with compounds of formula I or that very slight damage to the crop occurs only when very high dosages are used. The compounds of formula I are therefore valuable selective herbicides in crops of useful plants such as cereals, sugar beet, rape, soybeans, rice and maize. A wide range of application rates can be used particularly in rice crops, especially when the rice crops concerned are transplanted rice and the compounds of formula I are applied after transplantation.

The active ingredients of formula I are customarily used at application rates of from 0.01 to 5 kg of active ingredient per hectare in order to achieve satisfactory results. Where environmental conditions require it, the application rates may in suitable cases exceed the limits indicated above. The preferred application rates are, however, generally from 0.02 kg to 1.0 kg of active ingredient per hectare.

In the definitions, alkyl is to be understood as being straight-chain or branched alkyl; for example methyl, ethyl, n-propyl, isopropyl or the four butyl isomers. Alkoxy is to be understood as being: methoxy, ethoxy, propoxy or the four butoxy isomers, but especially methoxy, ethoxy or isopropoxy. Alkylthio is methylthio, ethylthio, propylthio, isopropylthio or butylthio, but especially methylthio.

In the above definitions, halogen is fluorine, chlorine, bromine or iodine, with fluorine and chlorine being preferred. Alkenyl is, for example, vinyl, allyl, 1-methylvinyl, 3-butenyl, 2-butenyl, 1-butenyl, 1-propenyl, methallyl or 3-methyl-2-butenyl, with vinyl, allyl and methallyl being preferred. Examples of alkynyl are ethynyl, 1-propynyl, propargyl, 1-butynyl, 2-butynyl or 3-butynyl, but preferably ethynyl or propargyl. Cycloalkyl is generally cyclopropyl, cyclobutyl, cyclopentyl, cyclohexyl or cycloheptyl, preferably cyclopentyl or cyclohexyl. Radicals that can be formed by combination of the given meanings, such as haloalkyl, haloalkoxy, alkoxyalkyl, haloalkylthio or haloalkylcarbonyl, have the appropriate combinations of specific group members. Important examples thereof are: trifluoromethyl, chloromethyl, 2,2,2-trifluoroethyl, trifluoromethoxy, difluoromethoxy, 2,2,2-trifluoroethoxy, 2-chloroethoxy, methoxymethyl, methoxyethyl, ethoxyethyl, difluoromethylthio, chloromethylcarbonyl, trifluoromethylcarbonyl or bromomethylcarbonyl.

The radicals X which are bonded via a nitrogen atom to the imidazole ring include the following fundamental structures which may in turn be in unsubstituted form or may carry the mentioned substituents $R^2$, $R^3$, $R^4$, $R^5$, $R^6$, $R^7$ and $R^{14}$. In the cases where two aliphatic ring systems are linked, both the cis- and the trans-ring linkage forms are included.

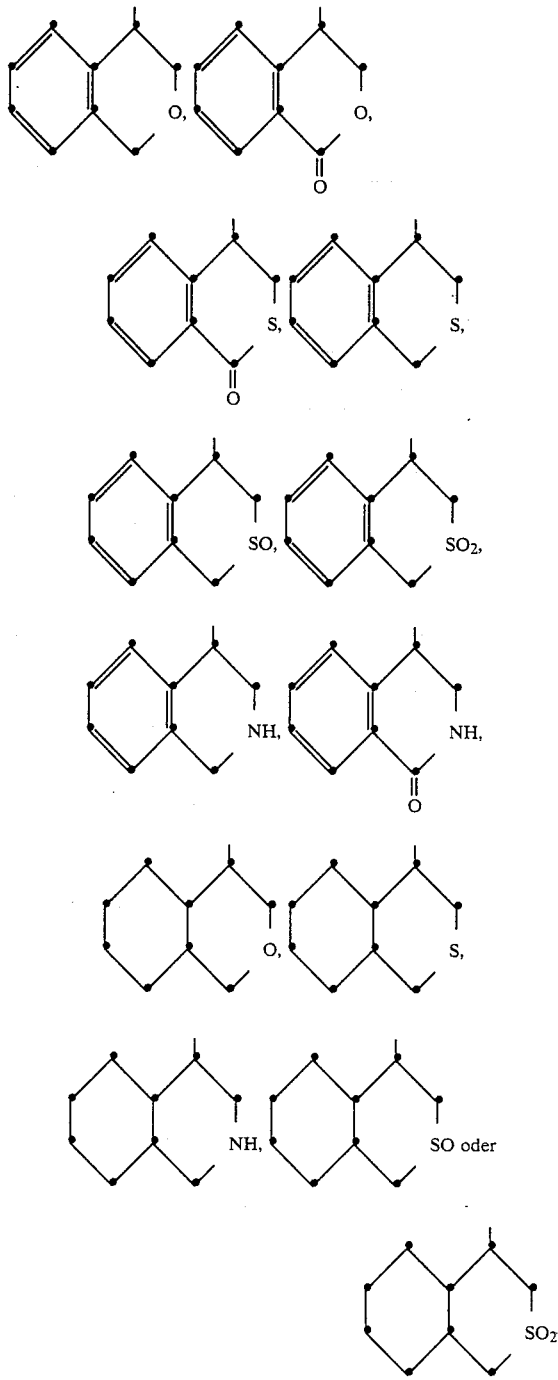

The radicals $R^2$ and $R^3$ are bonded to the same carbon atom. They can thus form a spirocyclic ring together with that carbon atom. Typical examples of such spirocyclic rings are cyclopropane, cyclobutane, cyclopentane, cyclohexane and cycloheptane rings.

The invention relates also to the salts that can be formed by the compounds of formula I with organic or inorganic bases, such as amines, alkali metal bases and alkaline earth metal bases, or quaternary ammonium bases or with organic or inorganic acids, such as mineral acids, sulfonic acids, carboxylic acids or phosphorus-containing acids.

Examples of salt-forming mineral acids are hydrofluoric acid, hydrochloric acid, hydrobromic acid, hydriodic acid, sulfuric acid, nitric acid, chloric acid, perchloric acid or phosphoric acid. Preferred saltforming sulfonic acids are toluenesulfonic acids, benzenesulfonic acid, methanesulfonic acid or trifluoromethanesulfonic acid. Preferred salt-forming carboxylic acids are acetic acid, trifluoroacetic acid, benzoic acid, chloroacetic acid, phthalic acid, maleic acid, malonic acid and citric acid. Phosphorus-containing acids are the various phosphonic acids, phosphonous acids and phosphinic acids.

Preferred salt-forming alkali metal hydroxides and alkaline earth metal hydroxides are the hydroxides of lithium, sodium, potassium, magnesium or calcium, but especially those of sodium or potassium. Examples of suitable salt-forming amines are primary, secondary and tertiary aliphatic and aromatic amines, such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, but especially isopropylamine, diethanolamine and 1,4-diazabicyclo[2.2.2]-octane. Examples of quaternary ammonium bases are generally the cations of haloammonium salts, for example the tetramethylammonium cation, the trimethylethylammonium cation, the tetraethylammonium cation, the trimethylethylammonium cation and also the ammonium cation.

The invention includes all optical isomers of compounds of formula I. These may occur when the radical X in position 1 of the imidazole ring and/or the group L in compounds of formula I contain asymmetrically substituted carbon atoms. Unless defined otherwise, the chemical names of compounds include mixtures of all their stereochemically isomeric forms. The mixtures contain all diastereoisomers and enantiomers of the basic molecular structure.

The pure isomeric forms of these optically active compounds can be obtained from the mixtures by customary separation methods. If, in an individual case, a specific stereochemical form is desired, this compound is preferably prepared by stereoselective synthesis processes. In these processes it is advantageous to use pure forms of the optically active starting materials.

Preferred compounds of formula I are those in which either (a) $R^1$ is hydrogen, or
(b) L is —$COOR^8$, —$CONR^9R^{10}$ or —CO—$R^{11}$, or
(c) X is the radical

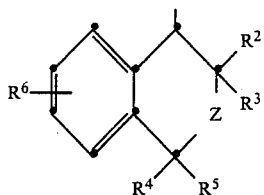

in which each of $R^2$ and $R^3$, independently of the other, is hydrogen or $C_1$-$C_4$alkyl, $R^4$ and $R^5$ are hydrogen or together form an oxo function, $R^6$ is hydrogen, $C_1$-$C_4$alkyl, $C_1$-$C_4$alkoxy or halogen, and Z is oxygen, —NH—, —NCH$_3$— or sulfur, or (d) X is the radical

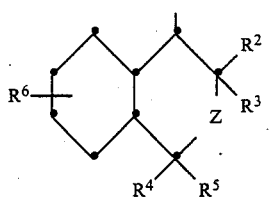

in which the ring linkage is in the trans-position, each of $R^2$ and $R^3$, independently of the other, is hydrogen or $C_1$-$C_4$alkyl, $R^4$ and $R^5$ are hydrogen, $R^6$ is hydrogen, $C_1$-$C_4$alkyl or halogen, and Z is oxygen, —NH—, —NCH$_3$— or sulfur.

Preferred compounds of group (b) are those subgroups in which either L is $C_1$-$C_4$alkoxycarbonyl or $C_1$-$C_4$alkylcarbonyl or —CO—NR$^9$R$^{10}$ wherein each of $R^9$ and $R^{10}$, independently of the other, is hydrogen or $C_1$-$C_4$alkyl.

Preferred compounds of group (c) are those in which $R^1$ is hydrogen and L is $C_1$-$C_4$alkoxycarbonyl, $C_1$-$C_4$alkylcarbonyl, carbamoyl, methylcarbamoyl or dimethylcarbamoyl.

Preferred compounds of group (d) are those in which $R^1$ is hydrogen and L is $C_1$-$C_4$alkoxycarbonyl, $C_1$-$C_4$alkylcarbonyl, carbamoyl, methylcarbamoyl or dimethylcarbamoyl.

The following preferred individual compounds of the present invention may be mentioned:

1-(3-methylisochroman-4-yl)-5-imidazolecarboxylic acid methyl ester,
1-(3,3-dimethylisochroman-4-yl)-5-imidazolecarboxylic acid methyl ester,
1-(3-methylisothiochroman-4-yl)-5-imidazolecarboxylic acid methyl ester,
1-(3,3-dimethylisothiochroman-4-yl)-5-imidazolecarboxylic acid methyl ester,
1-(3-methyl-1,2,3,4-tetrahydroisoquinolin-4-yl)-5-imidazolecarboxylic acid methyl ester,
1-(2,3-dimethyl-1,2,3,4-tetrahydroisoquinolin-4-yl)-5-imidazolecarboxylic acid methyl ester,
1-(3,3-dimethyl-1,2,3,4-tetrahydroisoquinolin-4-yl)-5-imidazolecarboxylic acid methyl ester, and
1-(3,3-dimethyl-1-oxoisochroman-4-yl)-5-imidazolecarboxylic acid methyl ester.

The compounds of formula I according to the invention are generally prepared by the following methods.

According to a first process, compounds of formula I in which $R^1$ is hydrogen are obtained by condensing an amine of formula II $$X\text{---}NH_2 \qquad (II),$$

in which X has the meaning given under formula I, with an N-cyanoimidoformic acid ester of formula III $$R\text{---}O\text{---}CH\text{=}N\text{---}CN \qquad (III)$$

in which R is $C_1$-$C_4$alkyl, alkylating the resulting N-cyanoformamidine of formula IV $$X\text{---}NH\text{---}CH\text{=}N\text{---}CN \qquad (IV),$$

in which X has the meaning given under formula I, with a haloacetic acid ester of formula V $$\text{Hal}\text{---}CH_2\text{---}L \qquad (V),$$

in which Hal is chlorine or bromine and L is $C_1$-$C_6$alkoxycarbonyl, in the presence of a base, cyclising the resulting intermediate of formula VI

in which X has the meaning given under formula I and L is $C_1$-$C_6$alkoxycarbonyl, in the presence of a base to form the 4-aminoimidazole of formula VII

in which X has the meaning given under formula I and L is $C_1$-$C_6$alkoxycarbonyl, and converting this compound, with diazotisation and removal of nitrogen, into the product of formula I in which L is $C_1$-$C_6$alkoxycarbonyl and $R^1$ is hydrogen, and, if desired, derivatising the group L in the 5-position in accordance with the other meanings as defined under formula I.

The special advantage of this process is that it can be carried out in a single reaction vessel—without isolation of the intermediates. In addition, the first two reaction steps for the alkylation of the primary amine of formula II with the products of formulae III and V can be interchanged as desired.

In accordance with a second process, the compounds of formula I are obtained by alkylating the amine of formula II $$X\text{---}NH_2 \qquad (II),$$

in which X has the meaning given under formula I, with a haloacetic acid ester of formula V $$\text{Hal}\text{---}CH_2\text{---}L \qquad (V),$$

in which Hal is chlorine or bromine and L is $C_1$-$C_6$alkoxycarbonyl, in the presence of a base, formylating the resulting glycine ester of formula VIII $$X\text{---}NH\text{---}CH_2\text{---}L \qquad (VIII),$$

in which X has the meaning given under formula I and L is $C_1$-$C_6$alkoxycarbonyl, with formic acid in the presence of acetic anhydride, reacting the resulting intermediate of formula IX

(IX)

in which X has the meaning given under formula I and L is $C_1$-$C_6$alkoxycarbonyl, with a formic acid $C_1$-$C_4$alkyl ester in the presence of an alkali metal base, cyclising the resulting intermediate of formula X

(X)

in which X has the meaning given under formula I, L is $C_1$-$C_6$alkoxycarbonyl and M is an alkali metal cation, with thiocyanic acid to form the product of formula I in which $R^1$ is —SH and L is $C_1$-$C_6$alkoxycarbonyl, and, if desired, desulfurating this compound in the 2-position and, if desired, derivatising the group L in the 5-position in accordance with the other meanings as defined under formula I.

In the derivatisation of the $C_1$-$C_6$alkoxycarbonyl radical in the 5-position the modification is effected in known manner, for example by hydrolysis, esterification, transesterification, amidation, transamidation, oximation or reduction. If desired, it is also possible to effect salt formation at the basic nitrogen atom of the imidazole ring.

The cyano compound (L=—CN) is obtained by dehydrating the carboxylic acid amide (L=—CONH$_2$). Suitable agents for this purpose are, for example, phosphorus pentachloride, phosphorus oxychloride, thienyl chloride, phosphorus pentoxide and acetic anhydride. The reaction temperature depends upon the dehydrating agent chosen and is generally from +20° C. to +120° C. If required, it is also possible to add inert organic solvents. The esters, thiol esters or amide derivatives (L=—COOR$^8$, —COSR$^8$, —CONR$^9$R$^{10}$) can be prepared from the carboxylic acids (L=—COOH) or the activated compounds obtainable therefrom, such as acid halides or anhydrides or mixed anhydrides, by reaction with the corresponding alcohols, thiols or amine compounds. Esters and thiol esters may also be obtained by alkylation of the carboxylic acids with haloalkyl compounds in the presence of bases. The heterocyclic compounds of formula I having the group

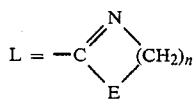

can be obtained by reaction of the corresponding carboxylic acids, or their activated representatives, such as their acid halides, with bifunctional compounds such as diamines, amino alcohols or aminothiols, according to processes known per se. The ketone derivatives (L=—CO—R$^{11}$) can be obtained from the esters by reduction to the aldehyde stage, alkylation to the secondary alcohol by means of Grignard addition and subsequent oxidation. The ether derivatives (L=—CH$_2$—O—R$^{12}$) can be obtained from the esters by reduction to the alcohol and, if desired, subsequent etherification.

The isothiochroman 2-oxides and isothiochroman 2,2-dioxides of formula I can be prepared by treatment of the corresponding isothiochromans or salts thereof of formula I with oxidising agents, such as, for example, hydrogen peroxide, m-chloroperbenzoic acid or sodium metaperiodate.

The compounds of formula I in which $R^4$ and $R^5$ together form an oxo function can be obtained from the corresponding compounds in which $R^4$ and $R^5$ are hydrogen by oxidation when $R^4$ and $R^5$ are bonded to a benzylic carbon atom, that is to say when the ring carrying $R^6$ and $R^7$ is aromatic. If the latter ring is saturated, the synthesis of the compounds in which $R^4$ and $R^5$ form an oxo function can be effected, for example, in accordance with the following synthesis scheme:

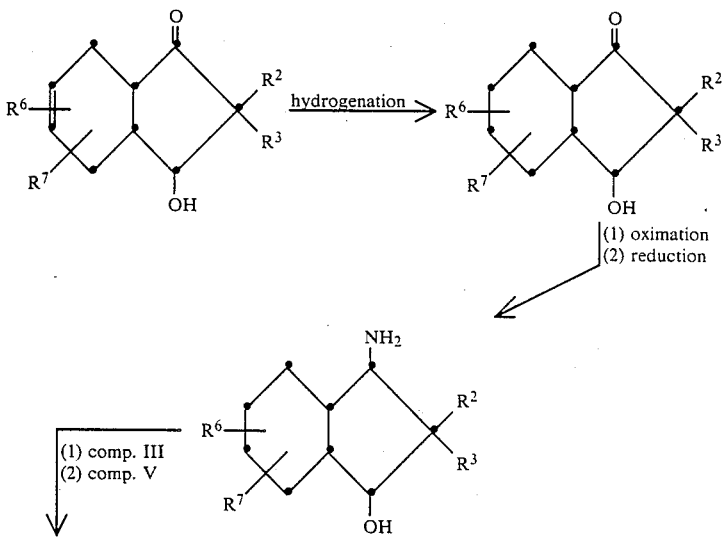

-continued

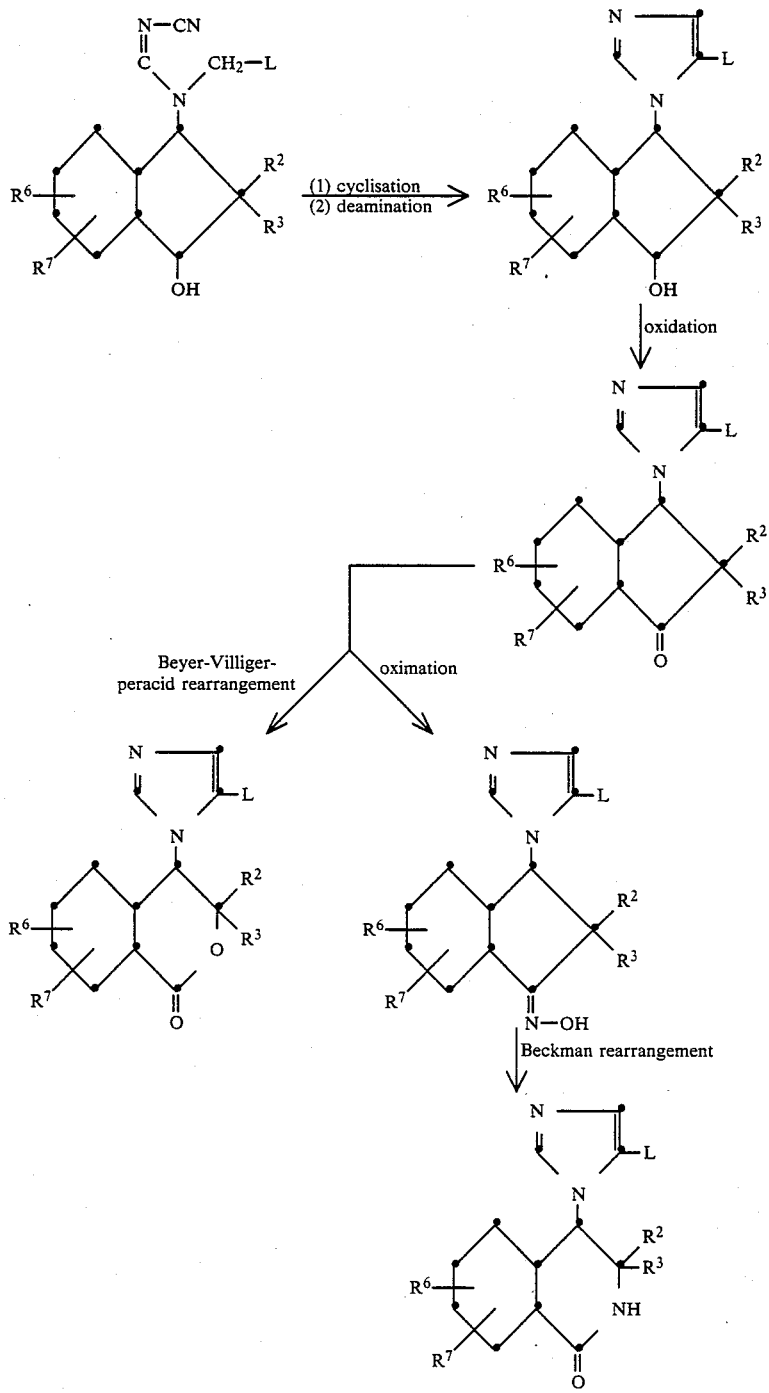

The individual reaction steps of this scheme are described in the literature in an analogous manner. The reaction conditions correspond to the customary conditions.

The intermediates of formula VII are novel. They have been developed especially for the synthesis of compounds of formula I, and the present invention therefore relates also to these. The majority of the amines of formula II are novel. The invention relates also to these novel compounds of formula II. They correspond to the formula II with the exception of the compounds: 4-amino-2-methyl-1,2,3,4-tetrahydroisoquinoline, 4-amino-2-ethyl-1,2,3,4-tetrahydroisoquinoline, 4-amino-2-benzyl-1,2,3,4-tetrahydroisoquinoline and 4-amino-7-methoxy-1,2,3,4-tetrahydroisoquinoline.

The individual reaction steps of the various processes can advantageously be carried out under the reaction conditions described below.

The condensation (II+III→IV) is advantageously carried out in a polar solvent, such as dimethylformamide or dimethyl acetamide, or in an alcohol of which the alkyl radical corresponds to the alkyl group of the N-cyanoimidoformic acid ester of formula III, at a temperature of from +20° C. to +80° C. In general the reaction takes place spontaneously and is exothermic.

The alkylation of the product of formula IV (IV+V→VI) is effected in the presence of a base as acid-binding agent. Such reagents can be both inorganic and organic bases. Examples thereof are alkali metal hydroxides, alkali metal hydrogen carbonates, alkali metal carbonates, alkaline earth metal oxides, alkaline earth metal carbonates, alkali metal alcoholates or tertiary amines, such as sodium hydroxide, potassium hydroxide, sodium carbonate, potassium hydrogen carbonate, magnesium oxide, calcium oxide, sodium methoxide, sodium ethoxide, potassium methoxide, potassium ethoxide, potassium tert.-butoxide, pyridine, triethylamine etc.. The reaction temperature is generally from 0° C. to +80° C., preferably from +10° C. to +50° C. If the reaction is to be carried out in a solvent, polar aprotic solvents are especially suitable for the alkylation, such as dimethylformamide, dimethyl acetamide or dimethyl sulfoxide.

The cyclisation of the intermediates of formula VI to form the 4-aminoimidazoles of formula VII is preferably carried out with base catalysis at elevated temperatures. Suitable conditions obtain when the operation is carried out by heating the compound of formula VI to boiling in an alcohol corresponding to that used for esterifying the alkoxycarbonyl group, in the presence of a catalytic amount of the alcoholate produced by dissolution of an alkali metal. The reaction can, however, also be carried out by heating the compound of formula VI with the corresponding alcoholate in a polar solvent, such as dimethylformamide or dimethyl sulfoxide. The reaction temperature is generally from +60° C. to +140° C.

The deamination of the 4-position of the imidazole ring (VII→I) is advantageously effected by treating the 4-aminoimidazole with tert.-butyl nitrite in tetrahydrofuran, dioxane or dimethylformamide. The diazotisation of the amino group and subsequent removal of nitrogen can, however, also be carried out in an aqueous acidic medium with sodium nitrite in the presence of nitric acid, hydrochloric acid or sulfuric acid and by subsequent boiling with hypophosphorous acid $H_3PO_2$.

The preparation of the glycine ester of formula VIII (II+V→VIII) is carried out under reaction conditions the same as those in the process step (IV+V→VI) described above.

The formylation of the glycine ester of formula VIII using formic acid (VIII→IX) in the presence of a water-removing agent, such as acetic anhydride, is effected according to customary condensation conditions known per se for the preparation of carboxylic acid amides. Alternatively, the formylation can also be effected by reaction with formic acid in a water-separating apparatus by azeotropic removal of the water of reaction.

The condensation of the intermediates of formula IX with a formic acid alkyl ester in the presence of an alkali metal base is customarily carried out in an inert solvent. Alkali metal alcoholates or alkali metal hydrides have proved suitable as alkali metal bases. Examples thereof are sodium methoxide, potassium methoxide, potassium ethoxide, sodium ethoxide, sodium hydride or lithium hydride. Inert solvents are alcohols, such as methanol, ethanol or isopropanol, or ethers, such as diethyl ether, tetrahydrofuran or dioxane. The reaction temperatures is generally from −20° C. to +60° C., preferably from +10° C. to +40° C.

The process for the cyclisation of the enamine compound of formula X to form the products of formula I is advantageously carried out in an inert aqueous reaction system, for example in water or in a mixture of water with tetrahydrofuran or dioxane, at a temperature of from +50° C. to the boiling point of the solvent.

The desulfuration of products of formula I in which $R^1$ is —SH can be carried out, for example, by treatment with 15% nitrous acid at a temperature of from +20° C. to +40° C., or by treatment with nickel at a temperature of from +50° C. to +100° C.

If the synthesis of stereochemically pure isomers is required, it is advisable to select stereoselective reaction steps and conditions. Conversely, pure isomers can frequently by separated from the isomeric mixture by customary separation methods.

The starting materials of formulae III and V are known, or they can be prepared analogously to known compounds.

The preparation of the amines of formula II is effected by methods known in the literature, such as, for example, reduction of imines, oximes or oxime derivatives by catalytic or electrochemical methods or with metal hydrides, such as lithium aluminium hydride or sodium borohydride/titanium tetrachloride. A further possible method is the reductive amination of ketones by catalytic methods or with hydrides, such as sodium cyanoborohydride. The amines of formula II can also be obtained, starting from the ketones, by reaction with ammonium formate and subsequent hydrolysis of the N-formyl derivatives. This reaction is known in the literature as Leuckart-Wallach's amine preparation method.

The oximes required for the preparation of the amines of formula II are obtained by the reaction, known per se, of corresponding ketones with hydroxylamine. The oximes of formulae XI and XII

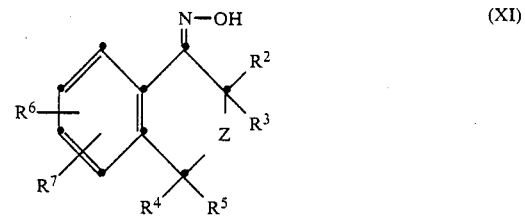

(XI)

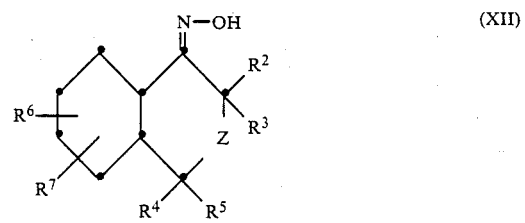

(XII)

in which Z, $R^2$, $R^3$, $R^4$, $R^5$, $R^6$ and $R^7$ have the meanings given under formula I, are novel with the exception of compounds of formula XI in which $R^2$ and $R^3$ both represent hydrogen.

Some of the ketones on which the oximes of formulae XI and XII are based are known. Likewise, in some cases the preparation of the ketones is described in the literature, such as, for example, isothiochromanone (J. Amer. Chem. Soc. 85, 2278 (1963)), substituted isothiochromanones (Bull. Soc. Chim. France 2225 (1961)), 2-isochroman-4-one (J. Org. Chem. 50, 2128 (1985)), 4-keto-1,2,3,4-tetrahydroisoquinoline (Advan. Heterocyclic Chem. 15, 99–136 (1973)) and 3-thiadecal-1-one (Recl. Trav. Chim. Pays-Bas 92, 937 (1973)) or it is effected in an analogous manner.

The compounds of formula I are stable and do not require special precautions for handling.

When the compound of formula I is used within the indicated range of application rates, these active ingredients are distinguished by good selective herbicidal properties which render them excellently suitable for use in crops of useful plants, especially sugar beet, soybeans, cereals and maize, and more especially rice. In some cases damage is caused even to weeds which could previously be combated only by the use of total herbicides. If application rates far exceeding the recommended range are used, then the development of all the plants treated is damaged to such an extent that the plants die.

The invention relates also to herbicidal compositions that contain the novel compounds of formula I. The invention relates also to methods of controlling weeds by the use of these novel compounds.

The compounds of formula I are used in unmodified form or, preferably, in the form of compositions together with the adjuvants conventionally employed in the art of formulation and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surfaceactive compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$-alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, as least one $C_8$–$C_{22}$-alkyl radical and, as further substituents, unsubstituted or halogenated lower alkyl, benzyl or hydroxylower alkyl radicals. The salts are preferably in the form of halides, methylsulfates or ethylsulfates, e.g. stearyl-trimethylammonium chloride or benzyldi(2-chloroethyl)ethylammonium bromide.

The surfactants customarily used in the art of formulation are described inter alia in the following publications:

"McCutcheon's Detergents and Emulsifiers Annual", MC Publishing Corp., Ridgewood, New Jersey, 1981;

H. Stache, "Tensid-Taschenbuch", 2nd Edition, C. Hanser Verlag, Munich, Vienna, 1981;

M. and J. Ash, "Encyclopaedia of Surfactants", Vol. I–III, Chemical Publishing Co., New York, 1980–1981.

The agrochemical compositions usually contain 0.1 to 95%, preferably 0.1 to 80%, of a compound of formula I, 1 to 99.9% of a solid or liquid adjuvant, and 0 and 25%, preferably 0.1 to 25%, of a surfactant.

Preferred formulations have especially the following compositions: (throughout percentages are by weight).

| Emulsifiable concentrates | |
|---|---|
| active ingredient | 1 to 20%, preferably 5 to 10% |
| surfactant | 5 to 30%, preferably 10 to 20% |
| liquid carrier | 50 to 94%, preferably 70 to 85% |
| Dusts | |
| active ingredient | 0.1 to 10%, preferably 0.1 to 1% |
| solid carrier | 99.9 to 90%, preferably 99.9 to 99% |
| Suspension concentrates | |
| active ingredient | 5 to 75%, preferably 10 to 50% |
| water | 94 to 25%, preferably 88 to 30% |
| surfactant | 1 to 40%, preferably 2 to 30% |
| Wettable powder | |
| active ingredient | 0.5 to 90%, preferably 1 to 80% |
| surfactant | 0.5 to 20%, preferably 1 to 15% |
| solid carrier | 5 to 99%, preferably 15 to 90% |
| Granulates | |
| active ingredient | 0.5 to 30%, preferably 3 to 15% |
| solid carrier | 99.5 to 70%, preferably 97 to 85% |

Whereas commercial products will preferably be formulated as concentrates, the end user will normally employ dilute formulations. The forms of application can be diluted down to 0.001% active ingredient.

The following Examples illustrate the present invention but do not represent a limitation thereof. The preparation examples show the methods by which the novel compounds of formula I can be obtained. The biological examples and the formulation examples demonstrate the use of the active ingredients for agrochemical purposes.

PREPARATION EXAMPLES:

Example P1:
1-(3,3-dimethylisothiochroman-4-yl)-5-imidazolecarboxylic acid methyl ester (Compound 1.016)

(a) 3,3-dimethylisothiochroman-4-oneoxime

A mixture of 10.0 g of 3,3-dimethylisothiochroman-4-one, 8.0 g of hydroxylamine hydrochloride, 18 ml of pyridine and 60 ml of ethanol is heated at reflux for 60 hours. The cooled reaction mixture is concentrated by evaporation, then toluene is added and the mixture is again concentrated by evaporation. The residue is boiled up in dichloromethane, cooled and filtered. The filtrate is concentrated by evaporation and the residue is chromatographed with silica gel (eluant: ethyl acetate/hexane 1:12). Concentration of the eluate by evaporation yields 6.0 g of 3,3-dimethylisothiochroman-4-oneoxime in the form of yellow crystals having a melting point of 83°–84° C.

(b) 4-amino-3,3-dimethylisothiochroman (Compound 7.04)

25.3 g of sodium borohydride in 435 ml of 1,2-dimethoxyethane are placed under a nitrogen atmosphere. 36.9 ml of titanium tetrachloride are added dropwise thereto at a temperature of from +15° to +18° C. The mixture is stirred for 3 hours at a temperature below +20° C. and then, at from +14° to +16° C., a solution of 33.0 g of 3,3-dimethylisothiochroman-4-oneoxime in 135 ml of 1,2-dimethoxyethane is added dropwise thereto. After stirring for 16 hours at room temperature, the mixture is poured onto ice-water and rendered basic with 30% aqueous ammonia solution. The mixture is then extracted twice with ether. The ether phases are washed with saturated sodium chloride solution, dried over sodium sulfate and concentrated by evaporation. Distillation of the residue yields 16.7 g of 4-amino-3,3-dimethylisothiochroman in the form of a colourless liquid having a boiling point of +80° C. at 0.06 mbar.

(c) N-cyano-N'-(3,3-dimethylisothiochroman-4-yl)-formamidine 10.0 g of N-cyanoimidoformic acid ethyl ester are added dropwise to 16.7 g of 4-amino-3,3-dimethylisothiochroman in 10 ml of dry ethanol. The exothermic reaction is complete after 2 hours. The mixture is cooled to 0° C., and the precipitate is filtered off and washed with a small amount of ethanol. After drying, 14.3 g of N-cyano-N'-(3,3-dimethylisothiochroman-4-yl)-formamidine are obtained in the form of colourless crystals having a melting point of 164°–166° C.

(d) N-cyano-N'-(3,3-dimethylisothiochroman-4yl)-N'-methoxycarbonylmethylformamidine 12.4 g of potassium tert.-butoxide are added to a mixture of 23.9 g of N-cyano-N'-(3,3-dimethylisothiochroman-4-yl)-formamidine and 18 ml of dimethyl sulfoxide. After a reaction period of 2.5 hours, 10.9 ml of bromoacetic acid methyl ester are added dropwise while cooling with ice-water. After stirring for 16 hours at room temperature, ice-water is added to the reaction mixture. Extraction with ether, washing of the organic phase with saturated sodium chloride solution and concentration of the organic phase by evaporation yield a residue, to which ether is added. The precipitate that forms is separated off and dried. 23.9 g of N-cyano-N'-(3,3-dimethylisothiochroman-4-yl)-N'-methoxycarbonylmethylformamidine having a melting point of 141°–143° C. are obtained.

(e) 4-amino-1-(3,3-dimethylisothiochroman-4-yl)-5-imidazolecarboxylic acid methyl ester (Compound 9.08)

23.0 g of N-cyano-N'-(3,3-dimethylisothiochroman-4-yl)N'-methoxycarbonylmethylformamidine are introduced into 35 ml of methanol and, after the addition of 2.6 ml of 30% methanolic sodium methoxide solution, heated at boiling for 16 hours. After cooling, the reaction solution is poured onto an ice-water/dichloromethane mixture. The organic phase is separated off, extracted with water and dried over sodium sulfate. Filtration and evaporation yield a brown oil which is boiled up with ether. After cooling and trituration, 18.3 g of 4-amino-1-(3,3-dimethylisothiochroman-4-yl)-5-imidazolecarboxylic acid methyl ester are obtained in the form of beige crystals.

(f) A solution of 5.0 g of 4-amino-1-(3,3-dimethylisothiochroman-4-yl)-5-imidazolecarboxylic acid methyl ester in 10 ml of tetrahydrofuran is added dropwise to a solution of 3.1 ml of tert.-butyl nitrite in 10 ml of tetrahydrofuran. After stirring for 16 hours at room temperature, the reaction mixture is poured onto ice-water. After extraction with ether, the organic phase is washed with saturated sodium chloride solution, dried over sodium sulfate, filtered and concentrated by evaporation. The residue is purified by chromatography on silica gel (eluant: ethyl acetate/hexane 2:5). There are thus obtained 3.2 g of 1-(3,3-dimethylisothiochroman-4-yl)-5-imidazolecarboxylic acid methyl ester in the form of a yellow resin which is caused to crystallise with hexane. The crystalline compound has a melting point of 108°–109° C.

The compounds of formula I listed in Tables 1 to 10, and their intermediates, are obtained in an analogous manner.

TABLE 1

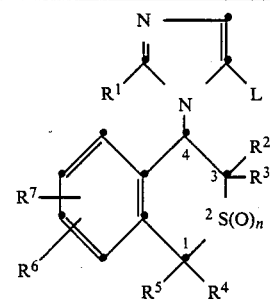

| Comp. No. | L | $R^1$ | $R^2$ | $R^3$ | n | $R^4$ | $R^5$ | $R^6$ | $R^7$ | physical data |
|---|---|---|---|---|---|---|---|---|---|---|
| 1.001 | $CO_2CH_3$ | H | H | H | 0 | H | H | H | H | |
| 1.002 | $CO_2CH_3$ | SH | H | H | 0 | H | H | H | H | |
| 1.003 | $CO_2CH_3$ | H | $CH_3$ | H | 0 | H | H | H | H | |
| 1.004 | $CO_2CH_3$ | H | $CH_3$ | H | 0 | H | H | H | H | 3,4-cis, m.p. 124–125° C. |
| 1.005 | $CO_2CH_3$ | H | $CH_3$ | H | 0 | H | H | H | H | 3,4-trans |
| 1.006 | $CO_2CH_3$ | H | $CH_3$ | H | 0 | =O | | H | H | |
| 1.007 | $CO_2CH_3$ | H | $CH_3$ | H | 0 | $CH_3$ | H | H | H | |
| 1.008 | $CO_2CH_3$ | H | $CH_3$ | H | 0 | $CH_3$ | $CH_3$ | H | H | |
| 1.009 | $CO_2CH_3$ | H | $CH_3$ | H | 0 | $CH_3$ | H | 5-$CH_3$ | H | |
| 1.010 | $CO_2CH_3$ | H | $CH_3$ | H | 0 | $CH_3$ | H | 5-F | H | |
| 1.011 | $CO_2CH_3$ | SH | $CH_3$ | H | 0 | $CH_3$ | H | H | H | |
| 1.012 | $CO_2CH_3$ | H | $CH_3$ | H | 0 | $CH_3$ | H | 6-$CH_3$ | H | |
| 1.013 | $CO_2CH_3$ | H | $CH_3$ | H | 0 | $CH_3$ | H | 6-$OCH_3$ | H | |
| 1.014 | $CO_2CH_3$ | H | $CH_3$ | H | 0 | $CH_3$ | H | 5-$CH_3$ | 8-$CH_3$ | |
| 1.015 | $CO_2CH_3$ | H | $CH_3$ | H | 0 | $C_2H_5$ | H | H | H | |
| 1.016 | $CO_2CH_3$ | H | $CH_3$ | $CH_3$ | 0 | H | H | H | H | m.p. 108–109° C. |
| 1.017 | $CO_2CH_3$ | SH | $CH_3$ | $CH_3$ | 0 | H | H | H | H | |
| 1.018 | $CO_2CH_3$ | H | $CH_3$ | $CH_3$ | 0 | $CH_3$ | H | H | H | |
| 1.019 | $CO_2CH_3$ | H | $CH_3$ | $CH_3$ | 0 | $CH_3$ | H | H | H | 1,4-cis |
| 1.020 | $CO_2CH_3$ | H | $CH_3$ | $CH_3$ | 0 | $CH_3$ | H | H | H | 1,4-trans |
| 1.021 | $CO_2CH_3$ | H | $CH_3$ | $CH_3$ | 0 | $CH_3$ | $CH_3$ | H | H | |
| 1.022 | $CO_2CH_3$ | H | $CH_3$ | $CH_3$ | 0 | $CH_3$ | H | 6-$CH_3$ | H | |
| 1.023 | $CO_2CH_3$ | H | $CH_3$ | $CH_3$ | 0 | H | H | 6-$CH_3$ | H | |
| 1.024 | $CO_2CH_3$ | H | $CH_3$ | $CH_3$ | 0 | H | H | 5-$CH_3$ | 8-$CH_3$ | |
| 1.025 | $CO_2CH_3$ | H | $CH_3$ | $CH_3$ | 0 | H | H | 7-$OCH_3$ | H | |
| 1.026 | $CO_2CH_3$ | H | $CH_3$ | $CH_3$ | 0 | H | H | 6-$OCH_3$ | H | |
| 1.027 | $CO_2CH_3$ | H | $CH_3$ | $CH_3$ | 0 | H | H | 6-F | H | |
| 1.028 | $CO_2CH_3$ | H | $CH_3$ | $CH_3$ | 0 | H | H | 6-Cl | H | |
| 1.029 | $CO_2CH_3$ | H | $CH_3$ | $CH_3$ | 0 | H | H | 6-Br | H | |
| 1.030 | $CO_2CH_3$ | H | $CH_3$ | $CH_3$ | 0 | H | H | 6-$NO_2$ | H | |
| 1.031 | $CO_2CH_3$ | H | $CH_3$ | $CH_3$ | 0 | H | H | 5-F | H | |
| 1.032 | $CO_2CH_3$ | H | $CH_3$ | $CH_3$ | 0 | H | H | 5-$CH_3$ | H | |
| 1.033 | $CO_2CH_3$ | H | $CH_3$ | $CH_3$ | 0 | H | H | 5-$OCH_3$ | H | |
| 1.034 | $CO_2CH_3$ | H | $CH_3$ | $CH_3$ | 0 | =O | | H | H | |
| 1.035 | $CO_2CH_3$ | H | —$CH_2$—$CH_2$— | | 0 | H | H | H | H | |
| 1.036 | $CO_2CH_3$ | SH | —$CH_2$—$CH_2$— | | 0 | H | H | H | H | |
| 1.037 | $CO_2CH_3$ | H | —$CH_2$—$CH_2$— | | 0 | $CH_3$ | H | H | H | |
| 1.038 | $CO_2CH_3$ | H | H | H | 0 | $CH_3$ | H | H | H | |
| 1.039 | $CO_2CH_3$ | H | H | H | 0 | $CH_3$ | H | H | H | 1,4-cis |
| 1.040 | $CO_2CH_3$ | H | H | H | 0 | $CH_3$ | H | H | H | 1,4-trans |
| 1.041 | $CO_2CH_3$ | H | H | H | 0 | $CH_3$ | $CH_3$ | H | H | |
| 1.042 | $CO_2CH_3$ | SH | H | H | 0 | $CH_3$ | $CH_3$ | H | H | |
| 1.043 | $CO_2CH_3$ | H | H | H | 0 | $C_2H_5$ | H | H | H | |
| 1.044 | $CO_2CH_3$ | H | $C_2H_5$ | H | 0 | H | H | H | H | |
| 1.045 | $CO_2CH_3$ | H | $C_2H_5$ | H | 0 | H | H | H | H | 3,4-cis m.p. 101–103° C. |
| 1.046 | $CO_2CH_3$ | H | $C_2H_5$ | H | 0 | H | H | H | H | 3,4-trans |
| 1.047 | $CO_2CH_3$ | H | $C_2H_5$ | $CH_3$ | 0 | H | H | H | H | |
| 1.048 | $CO_2CH_3$ | H | $C_2H_5$ | $C_2H_5$ | 0 | H | H | H | H | |

TABLE 1-continued

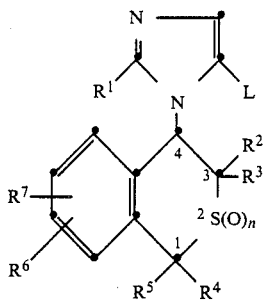

| Comp. No. | L | $R^1$ | $R^2$ | $R^3$ | n | $R^4$ | $R^5$ | $R^6$ | $R^7$ | physical data |
|---|---|---|---|---|---|---|---|---|---|---|
| 1.049 | $CO_2CH_3$ | SH | $C_2H_5$ | $C_2H_5$ | 0 | H | H | H | H | |
| 1.050 | $CO_2CH_3$ | H | $C_2H_5$ | $C_2H_5$ | 0 | =O | | H | H | |
| 1.051 | $CO_2CH_3$ | H | $C_2H_5$ | $C_2H_5$ | 0 | H | H | 6-$CH_3$ | H | |
| 1.052 | $CO_2CH_3$ | H | $C_2H_5$ | $C_2H_5$ | 0 | H | H | 6-F | H | |
| 1.053 | $CO_2CH_3$ | H | $C_2H_5$ | $C_2H_5$ | 0 | H | H | 5-$CH_3$ | H | |
| 1.054 | $CO_2CH_3$ | SH | $C_2H_5$ | $C_2H_5$ | 0 | H | H | 5-$CH_3$ | H | |
| 1.055 | $CO_2CH_3$ | H | $C_2H_5$ | $C_2H_5$ | 0 | $CH_3$ | H | H | H | |
| 1.056 | $CO_2CH_3$ | H | $C_2H_5$ | H | 0 | $CH_3$ | H | H | H | |
| 1.057 | $CO_2CH_3$ | H | $C_2H_5$ | H | 0 | $C_2H_5$ | H | H | H | |
| 1.058 | $CO_2CH_3$ | H | $C_2H_5$ | H | 0 | $C_2H_5$ | H | 6-$CH_3$ | H | |
| 1.059 | $CO_2CH_3$ | H | $C_2H_5$ | $C_2H_5$ | 0 | $C_2H_5$ | $CH_3$ | H | H | |
| 1.060 | $CO_2CH_3$ | H | $C_2H_5$ | $C_2H_5$ | 0 | $CH_3$ | $CH_3$ | H | H | |
| 1.061 | $CO_2CH_3$ | H | $C_3H_7$—n | H | 0 | H | H | H | H | |
| 1.062 | $CO_2CH_3$ | H | $C_3H_7$—i | H | 0 | H | H | H | H | |
| 1.063 | $CO_2CH_3$ | H | $C_3H_7$—i | H | 0 | $CH_3$ | H | H | H | |
| 1.064 | $CO_2CH_3$ | H | —$(CH_2)_4$— | | 0 | H | H | H | H | |
| 1.065 | $CO_2CH_3$ | H | —$(CH_2)_4$— | | 0 | $CH_3$ | H | H | H | |
| 1.066 | $CO_2CH_3$ | SH | —$(CH_2)_4$— | | 0 | H | H | H | H | |
| 1.067 | $CO_2CH_3$ | H | $CH_2CH=CH_2$ | H | 0 | H | H | H | H | |
| 1.068 | $CO_2CH_3$ | H | $CH_2CH=CH_2$ | $CH_3$ | 0 | H | H | H | H | |
| 1.069 | $CO_2CH_3$ | H | $C_4H_9$—n | H | 0 | H | H | H | H | |
| 1.070 | $CO_2CH_3$ | H | $CH_2$ | H | 0 | H | H | H | H | |
| 1.071 | $CO_2C_2H_5$ | H | $CH_3$ | H | 0 | H | H | H | H | |
| 1.072 | $CO_2C_2H_5$ | H | $CH_3$ | H | 0 | H | H | H | H | 3,4-cis |
| 1.073 | $CO_2C_2H_5$ | H | $CH_3$ | H | 0 | H | H | H | H | 3,4-trans |
| 1.074 | $CO_2C_2H_5$ | SH | $CH_3$ | H | 0 | $CH_3$ | H | H | H | |
| 1.075 | $CO_2C_2H_5$ | H | $CH_3$ | H | 0 | =O | | H | H | |
| 1.076 | $CO_2C_2H_5$ | H | $CH_3$ | H | 0 | $CH_3$ | H | H | H | |
| 1.077 | $CO_2C_2H_5$ | H | $CH_3$ | H | 0 | H | H | 5-$CH_3$ | H | |
| 1.078 | $CO_2C_2H_5$ | H | $CH_3$ | H | 0 | H | H | 6-$CH_3$ | H | |
| 1.079 | $CO_2C_2H_5$ | H | $CH_3$ | $CH_3$ | 0 | H | H | H | H | |
| 1.080 | $CO_2C_2H_5$ | H | $CH_3$ | $CH_3$ | 0 | $CH_3$ | H | H | H | |
| 1.081 | $CO_2C_2H_5$ | SH | $CH_3$ | $CH_3$ | 0 | H | H | H | H | |
| 1.082 | $CO_2C_2H_5$ | H | $CH_3$ | $CH_3$ | 0 | =O | | H | H | |
| 1.083 | $CO_2C_2H_5$ | H | $CH_3$ | $CH_3$ | 0 | H | H | 5-$CH_3$ | H | |
| 1.084 | $CO_2C_2H_5$ | H | $CH_3$ | $CH_3$ | 0 | H | H | 5-F | H | |
| 1.085 | $CO_2C_2H_5$ | H | $CH_3$ | $CH_3$ | 0 | H | H | 6-$CH_3$ | H | |
| 1.086 | $CO_2C_2H_5$ | SH | —$CH_2$—$CH_2$— | | 0 | H | H | H | H | |
| 1.087 | $CO_2C_2H_5$ | SH | —$CH_2$—$CH_2$— | | 0 | H | H | H | H | |
| 1.088 | $CO_2C_2H_5$ | H | $C_2H_5$ | H | 0 | H | H | H | H | |
| 1.089 | $CO_2C_2H_5$ | H | $C_2H_5$ | H | 0 | H | H | H | H | 3,4-cis |
| 1.090 | $CO_2C_2H_5$ | H | $C_2H_5$ | H | 0 | H | H | H | H | 3,4-trans |
| 1.091 | $CO_2C_2H_5$ | H | $C_2H_5$ | H | 0 | $CH_3$ | H | H | H | |
| 1.092 | $CO_2C_2H_5$ | H | $C_2H_5$ | $C_2H_5$ | 0 | H | H | H | H | |
| 1.093 | $CO_2C_2H_5$ | H | $C_2H_5$ | $C_2H_5$ | 0 | $CH_3$ | H | H | H | |
| 1.094 | $CO_2C_2H_5$ | SH | $C_2H_5$ | $C_2H_5$ | 0 | H | H | H | H | |
| 1.095 | $CO_2C_2H_5$ | H | $C_2H_5$ | $C_2H_5$ | 0 | $C_2H_5$ | H | H | H | |
| 1.096 | $CO_2C_2H_5$ | H | $C_2H_5$ | $C_2H_5$ | 0 | =O | | H | H | |
| 1.097 | $COCH_3$ | H | $CH_3$ | H | 0 | H | H | H | H | |
| 1.098 | $COCH_3$ | H | $CH_3$ | H | 0 | H | H | H | H | 3,4-cis |
| 1.099 | $COCH_3$ | H | $CH_3$ | H | 0 | H | H | H | H | 3,4-trans |
| 1.100 | $COCH_3$ | SH | $CH_3$ | H | 0 | H | H | H | H | |
| 1.101 | $COCH_3$ | H | $CH_3$ | H | 0 | $CH_3$ | H | H | H | |
| 1.102 | $COCH_3$ | H | $CH_3$ | $CH_3$ | 0 | H | H | H | H | |
| 1.103 | $COCH_3$ | SH | $CH_3$ | $CH_3$ | 0 | H | H | H | H | |
| 1.104 | $COCH_3$ | H | —$CH_2$—$CH_2$— | | 0 | H | H | H | H | |
| 1.105 | $COCH_3$ | H | $C_2H_5$ | H | 0 | H | H | H | H | |
| 1.106 | $COCH_3$ | H | $C_2H_5$ | $C_2H_5$ | 0 | H | H | H | H | |
| 1.107 | $COCH_3$ | H | $C_2H_5$ | H | 0 | $CH_3$ | H | H | H | |
| 1.108 | $COCH_3$ | H | $C_2H_5$ | $C_2H_5$ | 0 | =O | | H | H | |
| 1.109 | $COC_2H_5$ | H | $CH_3$ | H | 0 | H | H | H | H | |
| 1.110 | $COC_2H_5$ | H | $CH_3$ | $CH_3$ | 0 | H | H | H | H | |
| 1.111 | $COC_2H_5$ | H | $CH_3$ | $CH_3$ | 0 | $CH_3$ | H | H | H | |
| 1.112 | $COC_2H_5$ | H | —$CH_2$—$CH_2$— | | 0 | $CH_3$ | H | H | H | |
| 1.113 | $COC_2H_5$ | H | $C_2H_5$ | H | 0 | H | H | H | H | |

TABLE 1-continued

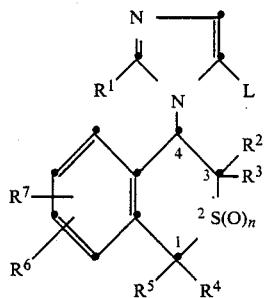

| Comp. No. | L | R¹ | R² | R³ | n | R⁴ | R⁵ | R⁶ | R⁷ | physical data |
|---|---|---|---|---|---|---|---|---|---|---|
| 1.114 | COC₂H₅ | H | C₂H₅ | C₂H₅ | 0 | H | H | H | H | |
| 1.115 | CONH₂ | H | CH₃ | H | 0 | H | H | H | H | |
| 1.116 | CONH₂ | H | CH₃ | CH₃ | 0 | H | H | H | H | |
| 1.117 | CONH₂ | H | —CH₂—CH₂— | | 0 | H | H | H | H | |
| 1.118 | CONH₂ | H | C₂H₅ | H | 0 | H | H | H | H | |
| 1.119 | CONH₂ | H | C₂H₅ | C₂H₅ | 0 | H | H | H | H | |
| 1.120 | CONHCH₃ | H | CH₃ | H | 0 | H | H | H | H | |
| 1.121 | CONHCH₃ | H | CH₃ | CH₃ | O | H | H | H | H | |
| 1.122 | CONHCH₃ | H | —CH₂—CH₂— | | 0 | H | H | H | H | |
| 1.123 | CONHCH₃ | H | C₂H₅ | H | 0 | H | H | H | H | |
| 1.124 | CONHCH₃ | H | C₂H₅ | C₂H₅ | 0 | H | H | H | H | |
| 1.125 | CON(CH₃)₂ | H | CH₃ | H | 0 | H | H | H | H | |
| 1.126 | CON(CH₃)₂ | H | CH₃ | CH₃ | 0 | H | H | H | H | |
| 1.127 | CON(CH₃)₂ | H | —CH₂—CH₂— | | 0 | H | H | H | H | |
| 1.128 | CON(CH₃)₂ | H | C₂H₅ | H | 0 | H | H | H | H | |
| 1.129 | CON(CH₃)₂ | H | C₂H₅ | C₂H₅ | 0 | H | H | H | H | |
| 1.130 | CN | H | CH₃ | CH₃ | 0 | H | H | H | H | |
| 1.131 | CO₂CH₂CH=CH₂ | H | CH₃ | CH₃ | 0 | H | H | H | H | |
| 1.132 | CO₂CH₂CH=CH | H | CH₃ | CH₃ | 0 | H | H | H | H | |
| 1.133 | CO₂C₃H₇ | H | CH₃ | CH₃ | 0 | H | H | H | H | |
| 1.134 | CONHOCH₃ | H | CH₃ | CH₃ | 0 | H | H | H | H | |
| 1.135 | CO₂CH₃ | H | CH₃ | H | 1 | H | H | H | H | |
| 1.136 | CO₂CH₃ | H | CH₃ | H | 1 | H | H | H | H | 2,3-cis |
| 1.137 | CO₂CH₃ | H | CH₃ | H | 1 | H | H | H | H | 2,3-trans |
| 1.138 | CO₂CH₃ | H | CH₃ | CH₃ | 1 | H | H | H | H | |
| 1.139 | CO₂CH₃ | H | —CH₂—CH₂— | | 1 | H | H | H | H | |
| 1.140 | CO₂CH₃ | H | C₂H₅ | H | 1 | H | H | H | H | |
| 1.141 | CO₂CH₃ | H | C₂H₅ | C₂H₅ | 1 | H | H | H | H | |
| 1.142 | CO₂C₂H₅ | H | CH₃ | CH₃ | 1 | H | H | H | H | |
| 1.143 | COCH₃ | H | CH₃ | CH₃ | 1 | H | H | H | H | |
| 1.144 | CO₂C₂H₅ | H | CH₃ | CH₃ | 1 | H | H | H | H | |
| 1.145 | CONHCH₃ | H | CH₃ | CH₃ | 1 | H | H | H | H | |
| 1.146 | CON(CH₃)₂ | H | CH₃ | CH₃ | 1 | H | H | H | H | |
| 1.147 | CN | H | CH₃ | CH₃ | 1 | H | H | H | H | |
| 1.148 | CO₂CH₃ | H | CH₃ | H | 2 | H | H | H | H | |
| 1.149 | CO₂CH₃ | H | CH₃ | H | 2 | H | H | H | H | 3,4-cis |
| 1.150 | CO₂CH₃ | H | CH₃ | H | 2 | H | H | H | H | 3,4-trans |
| 1.151 | CO₂CH₃ | H | CH₃ | CH₃ | 2 | H | H | H | H | m.p. 171–173° C. |
| 1.152 | CO₂CH₃ | H | C₂H₅ | H | 2 | H | H | H | H | |
| 1.153 | CO₂CH₃ | H | C₂H₅ | C₂H₅ | 2 | H | H | H | H | |
| 1.154 | CO₂CH₃ | H | H | H | 2 | CH₃ | H | H | H | |
| 1.155 | CO₂C₂H₅ | H | CH₃ | CH₃ | 2 | H | H | H | H | |
| 1.156 | COCH₃ | H | CH₃ | CH₃ | 2 | H | H | H | H | |
| 1.157 | COC₂H₅ | H | CH₃ | CH₃ | 2 | H | H | H | H | |
| 1.158 | CONHCH₃ | H | CH₃ | CH₃ | 2 | H | H | H | H | |
| 1.159 | CON(CH₃)₂ | H | CH₃ | CH₃ | 2 | H | H | H | H | |
| 1.160 | CN | H | CH₃ | CH₃ | 2 | H | H | H | H | |

TABLE 2

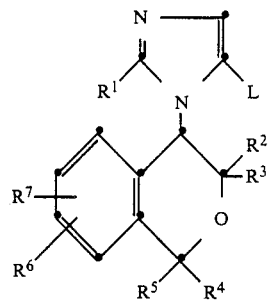

| Comp. No. | L | R¹ | R² | R³ | R⁴ | R⁵ | R⁶ | R⁷ | physical data |
|---|---|---|---|---|---|---|---|---|---|
| 2.001 | $CO_2CH_3$ | H | H | H | H | H | H | H | m.p. 48–50° C. |
| 2.002 | $CO_2CH_3$ | SH | H | H | H | H | H | H | |
| 2.003 | $CO_2CH_3$ | H | $CH_3$ | H | H | H | H | H | |
| 2.004 | $CO_2CH_3$ | H | $CH_3$ | H | H | H | H | H | 3,4-cis |
| 2.005 | $CO_2CH_3$ | H | $CH_3$ | H | H | H | H | H | 3,4-trans |
| 2.006 | $CO_2CH_3$ | H | $CH_3$ | H | =O | | H | H | |
| 2.007 | $CO_2CH_3$ | H | $CH_3$ | H | $CH_3$ | H | H | H | |
| 2.008 | $CO_2CH_3$ | H | $CH_3$ | H | $CH_3$ | $CH_3$ | H | H | |
| 2.009 | $CO_2CH_3$ | H | $CH_3$ | H | $CH_3$ | H | 5-$CH_3$ | H | |
| 2.010 | $CO_2CH_3$ | H | $CH_3$ | H | $CH_3$ | H | 5-F | H | |
| 2.011 | $CO_2CH_3$ | SH | $CH_3$ | H | $CH_3$ | H | H | H | |
| 2.012 | $CO_2CH_3$ | H | $CH_3$ | H | $CH_3$ | H | 6-$CH_3$ | H | |
| 2.013 | $CO_2CH_3$ | H | $CH_3$ | H | $CH_3$ | H | 6-$OCH_3$ | H | |
| 2.014 | $CO_2CH_3$ | H | $CH_3$ | H | $CH_3$ | H | 5-$CH_3$ | 8-$CH_3$ | |
| 2.015 | $CO_2CH_3$ | H | $CH_3$ | H | $C_2H_5$ | H | H | H | |
| 2.016 | $CO_2CH_3$ | H | $CH_3$ | $CH_3$ | H | H | H | H | m.p. 110–112° C. |
| 2.017 | $CO_2CH_3$ | SH | $CH_3$ | $CH_3$ | H | H | H | H | |
| 2.018 | $CO_2CH_3$ | H | $CH_3$ | $CH_3$ | $CH_3$ | H | H | H | |
| 2.019 | $CO_2CH_3$ | H | $CH_3$ | $CH_3$ | $CH_3$ | H | H | H | 1,4-cis |
| 2.020 | $CO_2CH_3$ | H | $CH_3$ | $CH_3$ | $CH_3$ | H | H | H | 1,4-trans |
| 2.021 | $CO_2CH_3$ | H | $CH_3$ | $CH_3$ | $CH_3$ | $CH_3$ | H | H | |
| 2.022 | $CO_2CH_3$ | H | $CH_3$ | $CH_3$ | $CH_3$ | H | 6-$CH_3$ | H | |
| 2.023 | $CO_2CH_3$ | H | $CH_3$ | $CH_3$ | H | H | 6-$CH_3$ | H | |
| 2.024 | $CO_2CH_3$ | H | $CH_3$ | $CH_3$ | H | H | 5-$CH_3$ | 8-$CH_3$ | |
| 2.025 | $CO_2CH_3$ | H | $CH_3$ | $CH_3$ | H | H | 7-$OCH_3$ | H | |
| 2.026 | $CO_2CH_3$ | H | $CH_3$ | $CH_3$ | H | H | 6-$OCH_3$ | H | |
| 2.027 | $CO_2CH_3$ | H | $CH_3$ | $CH_3$ | H | H | 6-F | H | |
| 2.028 | $CO_2CH_3$ | H | $CH_3$ | $CH_3$ | H | H | 6-Cl | H | |
| 2.029 | $CO_2CH_3$ | H | $CH_3$ | $CH_3$ | H | H | 6-Br | H | |
| 2.030 | $CO_2CH_3$ | H | $CH_3$ | $CH_3$ | H | H | 6-$NO_2$ | H | |
| 2.031 | $CO_2CH_3$ | H | $CH_3$ | $CH_3$ | H | H | 5-F | H | |
| 2.032 | $CO_2CH_3$ | H | $CH_3$ | $CH_3$ | H | H | 5-$CH_3$ | H | |
| 2.033 | $CO_2CH_3$ | H | $CH_3$ | $CH_3$ | H | H | 5-$OCH_3$ | H | |
| 2.034 | $CO_2CH_3$ | H | $CH_3$ | $CH_3$ | =O | | H | H | m.p. 123–125° C. |
| 2.035 | $CO_2CH_3$ | H | —$CH_2$—$CH_2$— | | H | H | H | H | |
| 2.036 | $CO_2CH_3$ | SH | —$CH_2$—$CH_2$— | | H | H | H | H | |
| 2.037 | $CO_2CH_3$ | H | —$CH_2$—$CH_2$— | | $CH_3$ | H | H | H | |
| 2.038 | $CO_2CH_3$ | H | H | H | $CH_3$ | H | H | H | |
| 2.039 | $CO_2CH_3$ | H | H | H | $CH_3$ | H | H | H | 1,4-cis |
| 2.040 | $CO_2CH_3$ | H | H | H | $CH_3$ | H | H | H | 1,4-trans |
| 2.041 | $CO_2CH_3$ | H | H | H | $CH_3$ | $CH_3$ | H | H | |
| 2.042 | $CO_2CH_3$ | SH | H | H | $CH_3$ | $CH_3$ | H | H | |
| 2.043 | $CO_2CH_3$ | H | H | H | $C_2H_5$ | H | H | H | |
| 2.044 | $CO_2CH_3$ | H | $C_2H_5$ | H | H | H | H | H | |
| 2.045 | $CO_2CH_3$ | H | $C_2H_5$ | H | H | H | H | H | 3,4-cis |
| 2.046 | $CO_2CH_3$ | H | $C_2H_5$ | H | H | H | H | H | 3,4-trans |
| 2.047 | $CO_2CH_3$ | H | $C_2H_5$ | $CH_3$ | H | H | H | H | |
| 2.048 | $CO_2CH_3$ | H | $C_2H_5$ | $C_2H_5$ | H | H | H | H | |
| 2.049 | $CO_2CH_3$ | SH | $C_2H_5$ | $C_2H_5$ | H | H | H | H | |
| 2.050 | $CO_2CH_3$ | H | $C_2H_5$ | $C_2H_5$ | =O | | H | H | |
| 2.051 | $CO_2CH_3$ | H | $C_2H_5$ | $C_2H_5$ | H | H | 6-$CH_3$ | H | |
| 2.052 | $CO_2CH_3$ | H | $C_2H_5$ | $C_2H_5$ | H | H | 6-F | H | |
| 2.053 | $CO_2CH_3$ | H | $C_2H_5$ | $C_2H_5$ | H | H | 5-$CH_3$ | H | |
| 2.054 | $CO_2CH_3$ | SH | $C_2H_5$ | $C_2H_5$ | H | H | 5-$CH_3$ | H | |
| 2.055 | $CO_2CH_3$ | H | $C_2H_5$ | $C_2H_5$ | $CH_3$ | H | H | H | |
| 2.056 | $CO_2CH_3$ | H | $C_2H_5$ | H | $CH_3$ | H | H | H | |
| 2.057 | $CO_2CH_3$ | H | $C_2H_5$ | H | $C_2H_5$ | H | H | H | |
| 2.058 | $CO_2CH_3$ | H | $C_2H_5$ | H | $C_2H_5$ | H | 6-$CH_3$ | H | |
| 2.059 | $CO_2CH_3$ | H | $C_2H_5$ | $C_2H_5$ | $C_2H_5$ | $CH_3$ | H | H | |
| 2.060 | $CO_2CH_3$ | H | $C_2H_5$ | $C_2H_5$ | $CH_3$ | $CH_3$ | H | H | |
| 2.061 | $CO_2CH_3$ | H | $C_3H_7$—n | H | H | H | H | H | |
| 2.062 | $CO_2CH_3$ | H | $C_3H_7$—i | H | H | H | H | H | |
| 2.063 | $CO_2CH_3$ | H | $C_3H_7$—i | H | $CH_3$ | H | H | H | |
| 2.064 | $CO_2CH_3$ | H | —$(CH_2)_4$— | | H | H | H | H | |
| 2.065 | $CO_2CH_3$ | H | —$(CH_2)_4$— | | $CH_3$ | H | H | H | |

TABLE 2-continued

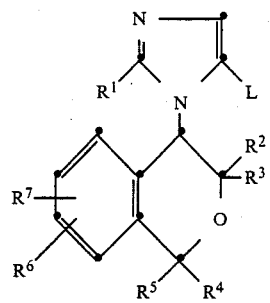

| Comp. No. | L | R¹ | R² | R³ | R⁴ | R⁵ | R⁶ | R⁷ | physical data |
|---|---|---|---|---|---|---|---|---|---|
| 2.066 | $CO_2CH_3$ | SH | —(CH$_2$)$_4$— | | H | H | H | H | |
| 2.067 | $CO_2CH_3$ | H | $CH_2CH=CH_2$ | H | H | H | H | H | |
| 2.068 | $CO_2CH_3$ | H | $CH_2CH=CH_2$ | $CH_3$ | H | H | H | H | |
| 2.069 | $CO_2CH_3$ | H | $C_4H_9$—n | H | H | H | H | H | |
| 2.070 | $CO_2CH_3$ | H | $CH_2$ | H | H | H | H | H | |
| 2.071 | $CO_2C_2H_5$ | H | $CH_3$ | H | H | H | H | H | |
| 2.072 | $CO_2C_2H_5$ | H | $CH_3$ | H | H | H | H | H | 3,4-cis |
| 2.073 | $CO_2C_2H_5$ | H | $CH_3$ | H | H | H | H | H | 3,4-trans |
| 2.074 | $CO_2C_2H_5$ | SH | $CH_3$ | H | $CH_3$ | H | H | H | |
| 2.075 | $CO_2C_2H_5$ | H | $CH_3$ | H | =O | | H | H | |
| 2.076 | $CO_2C_2H_5$ | H | $CH_3$ | H | $CH_3$ | H | H | H | |
| 2.077 | $CO_2C_2H_5$ | H | $CH_3$ | H | H | H | 5-$CH_3$ | H | |
| 2.078 | $CO_2C_2H_5$ | H | $CH_3$ | H | H | H | 6-$CH_3$ | H | |
| 2.079 | $CO_2C_2H_5$ | H | $CH_3$ | $CH_3$ | H | H | H | H | |
| 2.080 | $CO_2C_2H_5$ | H | $CH_3$ | $CH_3$ | $CH_3$ | H | H | H | |
| 2.081 | $CO_2C_2H_5$ | SH | $CH_3$ | $CH_3$ | H | H | H | H | |
| 2.082 | $CO_2C_2H_5$ | H | $CH_3$ | $CH_3$ | =O | | H | H | |
| 2.083 | $CO_2C_2H_5$ | H | $CH_3$ | $CH_3$ | H | H | 5-$CH_3$ | H | |
| 2.084 | $CO_2C_2H_5$ | H | $CH_3$ | $CH_3$ | H | H | 5-F | H | |
| 2.085 | $CO_2C_2H_5$ | H | $CH_3$ | $CH_3$ | H | H | 6-$CH_3$ | H | |
| 2.086 | $CO_2C_2H_5$ | SH | —$CH_2$—$CH_2$— | | H | H | H | H | |
| 2.087 | $CO_2C_2H_5$ | SH | —$CH_2$—$CH_2$— | | H | H | H | H | |
| 2.088 | $CO_2C_2H_5$ | H | $C_2H_5$ | H | H | H | H | H | |
| 2.089 | $CO_2C_2H_5$ | H | $C_2H_5$ | H | H | H | H | H | 3,4-cis |
| 2.090 | $CO_2C_2H_5$ | H | $C_2H_5$ | H | H | H | H | H | 3,4-trans |
| 2.091 | $CO_2C_2H_5$ | H | $C_2H_5$ | H | $CH_3$ | H | H | H | |
| 2.092 | $CO_2C_2H_5$ | H | $C_2H_5$ | $C_2H_5$ | H | H | H | H | |
| 2.093 | $CO_2C_2H_5$ | H | $C_2H_5$ | $C_2H_5$ | $CH_3$ | H | H | H | |
| 2.094 | $CO_2C_2H_5$ | SH | $C_2H_5$ | $C_2H_5$ | H | H | H | H | |
| 2.095 | $CO_2C_2H_5$ | H | $C_2H_5$ | $C_2H_5$ | $C_2H_5$ | H | H | H | |
| 2.096 | $CO_2C_2H_5$ | H | $C_2H_5$ | $C_2H_5$ | =O | | H | H | |
| 2.097 | $COCH_3$ | H | $CH_3$ | H | H | H | H | H | |
| 2.098 | $COCH_3$ | H | $CH_3$ | H | H | H | H | H | 3,4-cis |
| 2.099 | $COCH_3$ | H | $CH_3$ | H | H | H | H | H | 3,4-trans |
| 2.100 | $COCH_3$ | SH | $CH_3$ | H | H | H | H | H | |
| 2.101 | $COCH_3$ | H | $CH_3$ | H | $CH_3$ | H | H | H | |
| 2.102 | $COCH_3$ | H | $CH_3$ | $CH_3$ | H | H | H | H | |
| 2.103 | $COCH_3$ | SH | $CH_3$ | $CH_3$ | H | H | H | H | |
| 2.104 | $COCH_3$ | H | —$CH_2$—$CH_2$— | | H | H | H | H | |
| 2.105 | $COCH_3$ | H | $C_2H_5$ | H | H | H | H | H | |
| 2.106 | $COCH_3$ | H | $C_2H_5$ | $C_2H_5$ | H | H | H | H | |
| 2.107 | $COCH_3$ | H | $C_2H_5$ | H | $CH_3$ | H | H | H | |
| 2.108 | $COCH_3$ | H | $C_2H_5$ | $C_2H_5$ | =O | | H | H | |
| 2.109 | $COC_2H_5$ | H | $CH_3$ | H | H | H | H | H | |
| 2.110 | $COC_2H_5$ | H | $CH_3$ | $CH_3$ | H | H | H | H | |
| 2.111 | $COC_2H_5$ | H | $CH_3$ | $CH_3$ | $CH_3$ | H | H | H | |
| 2.112 | $COC_2H_5$ | H | —$CH_2$—$CH_2$— | | $CH_3$ | H | H | H | |
| 2.113 | $COC_2H_5$ | H | $C_2H_5$ | H | H | H | H | H | |
| 2.114 | $COC_2H_5$ | H | $C_2H_5$ | $C_2H_5$ | H | H | H | H | |
| 2.115 | $CONH_2$ | H | $CH_3$ | H | H | H | H | H | |
| 2.116 | $CONH_2$ | H | $CH_3$ | $CH_3$ | H | H | H | H | |
| 2.117 | $CONH_2$ | H | —$CH_2$—$CH_2$— | | H | H | H | H | |
| 2.118 | $CONH_2$ | H | $C_2H_5$ | H | H | H | H | H | |
| 2.119 | $CONH_2$ | H | $C_2H_5$ | $C_2H_5$ | H | H | H | H | |
| 2.120 | $CONHCH_3$ | H | $CH_3$ | H | H | H | H | H | |
| 2.121 | $CONHCH_3$ | H | $CH_3$ | $CH_3$ | H | H | H | H | |
| 2.122 | $CONHCH_3$ | H | —$CH_2$—$CH_2$— | | H | H | H | H | |
| 2.123 | $CONHCH_3$ | H | $C_2H_5$ | H | H | H | H | H | |
| 2.124 | $CONHCH_3$ | H | $C_2H_5$ | $C_2H_5$ | H | H | H | H | |
| 2.125 | $CON(CH_3)_2$ | H | $CH_3$ | H | H | H | H | H | |
| 2.126 | $CON(CH_3)_2$ | H | $CH_3$ | $CH_3$ | H | H | H | H | |
| 2.127 | $CON(CH_3)_2$ | H | —$CH_2$—$CH_2$— | | H | H | H | H | |
| 2.128 | $CON(CH_3)_2$ | H | $C_2H_5$ | H | H | H | H | H | |
| 2.129 | $CON(CH_3)_2$ | H | $C_2H_5$ | $C_2H_5$ | H | H | H | H | |
| 2.130 | CN | H | $CH_3$ | $CH_3$ | H | H | H | H | |

TABLE 2-continued

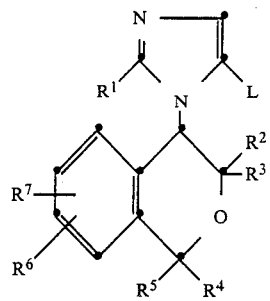

| Comp. No. | L | R¹ | R² | R³ | R⁴ | R⁵ | R⁶ | R⁷ | physical data |
|---|---|---|---|---|---|---|---|---|---|
| 2.131 | $CO_2CH_2CH=CH_2$ | H | $CH_3$ | $CH_3$ | H | H | H | H | |
| 2.132 | $CO_2CH_2C\equiv CH$ | H | $CH_3$ | $CH_3$ | H | H | H | H | |
| 2.133 | $CH_2-OH$ | H | $CH_3$ | $CH_3$ | H | H | H | H | Smp. 159–161° C. |

TABLE 3

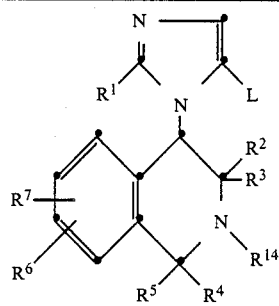

| Comp. No. | L | R¹ | R² | R³ | R¹⁴ | R⁴ | R⁵ | R⁶ | R⁷ | physical data |
|---|---|---|---|---|---|---|---|---|---|---|
| 3.01 | $CO_2CH_3$ | H | H | H | H | H | H | H | H | |
| 3.02 | $CO_2CH_3$ | H | H | H | H | =O | | H | H | |
| 3.03 | $CO_2CH_3$ | H | H | H | $CH_3$ | H | H | H | H | $n_D^{23}$: 1,5606 |
| 3.04 | $CO_2CH_3$ | H | H | H | Benzyl | H | H | H | H | |
| 3.05 | $CO_2CH_3$ | H | $CH_3$ | H | H | H | H | H | H | |
| 3.06 | $CO_2CH_3$ | H | $CH_3$ | H | H | H | H | H | H | 3,4-cis |
| 3.07 | $CO_2CH_3$ | H | $CH_3$ | H | H | H | H | H | H | 3,4-trans |
| 3.08 | $CO_2CH_3$ | H | $CH_3$ | H | $CH_3$ | H | H | H | H | |
| 3.09 | $CO_2CH_3$ | H | $CH_3$ | H | $CH_3$ | H | $CH_3$ | H | H | |
| 3.10 | $CO_2CH_3$ | H | $CH_3$ | H | H | H | $CH_3$ | H | H | |
| 3.11 | $CO_2CH_3$ | H | $CH_3$ | H | H | H | H | 6-$CH_3$ | H | |
| 3.12 | $CO_2CH_3$ | H | $CH_3$ | H | H | H | H | 6-$OCH_3$ | H | |
| 3.13 | $CO_2CH_3$ | H | $CH_3$ | H | H | H | H | 6-$OCH_3$ | 7-$OCH_3$ | |
| 3.14 | $CO_2CH_3$ | SH | $CH_3$ | H | $CH_3$ | H | H | H | H | |
| 3.15 | $CO_2CH_3$ | SH | $CH_3$ | $CH_3$ | H | H | H | H | H | |
| 3.16 | $CO_2CH_3$ | H | $CH_3$ | $CH_3$ | H | H | H | H | H | |
| 3.17 | $CO_2CH_3$ | H | $CH_3$ | $CH_3$ | H | =O | | H | H | |
| 3.18 | $CO_2CH_3$ | SH | $CH_3$ | $CH_3$ | $CH_3$ | H | H | H | H | |
| 3.19 | $CO_2CH_3$ | H | $CH_3$ | $CH_3$ | $CH_3$ | H | H | H | H | |
| 3.20 | $CO_2CH_3$ | H | $CH_3$ | $CH_3$ | $CH_3$ | =O | | H | H | |
| 3.21 | $CO_2CH_3$ | H | $CH_3$ | $CH_3$ | H | H | $CH_3$ | H | H | |
| 3.22 | $CO_2CH_3$ | H | $CH_3$ | $CH_3$ | $CH_3$ | H | H | 6-$CH_3$ | H | |
| 3.23 | $CO_2CH_3$ | H | $CH_3$ | $CH_3$ | H | H | H | 6-$OCH_3$ | 7-$OCH_3$ | |
| 3.24 | $CO_2CH_3$ | H | $C_2H_5$ | H | H | H | H | H | H | |
| 3.25 | $CO_2CH_3$ | H | $C_2H_5$ | H | $CH_3$ | H | H | H | H | |
| 3.26 | $CO_2CH_3$ | H | $C_2H_5$ | H | H | H | $CH_3$ | H | H | |
| 3.27 | $CO_2CH_3$ | H | $C_2H_5$ | $C_2H_5$ | H | H | H | H | H | |
| 3.28 | $CO_2CH_3$ | H | $C_2H_5$ | $C_2H_5$ | H | =O | | H | H | |
| 3.29 | $CO_2CH_3$ | H | $C_2H_5$ | $C_2H_5$ | $CH_3$ | H | H | H | H | |
| 3.30 | $CO_2CH_3$ | H | $C_2H_5$ | $C_2H_5$ | H | H | $CH_3$ | H | H | |
| 3.31 | $CO_2CH_3$ | SH | $C_2H_5$ | $C_2H_5$ | $CH_3$ | H | H | H | H | |
| 3.32 | $CO_2CH_3$ | H | —$CH_2$—$CH_2$— | | $CH_3$ | H | H | H | H | |
| 3.33 | $CO_2C_2H_5$ | H | H | H | H | H | H | H | H | |
| 3.34 | $CO_2C_2H_5$ | H | H | H | $CH_3$ | H | H | H | H | |
| 3.35 | $CO_2C_2H_5$ | H | $CH_3$ | H | H | H | H | H | H | |
| 3.36 | $CO_2C_2H_5$ | H | $CH_3$ | H | $CH_3$ | H | H | H | H | |
| 3.37 | $CO_2C_2H_5$ | H | $CH_3$ | H | $CH_3$ | H | $CH_3$ | H | H | |
| 3.38 | $CO_2C_2H_5$ | H | $CH_3$ | H | $CH_3$ | H | H | 6-$CH_3$ | H | |
| 3.39 | $CO_2C_2H_5$ | H | $CH_3$ | $CH_3$ | H | H | H | H | H | |
| 3.40 | $CO_2C_2H_5$ | H | $CH_3$ | $CH_3$ | H | =O | | H | H | |

TABLE 3-continued

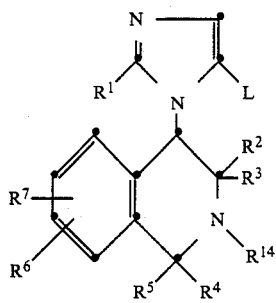

| Comp. No. | L | $R^1$ | $R^2$ | $R^3$ | $R^{14}$ | $R^4$ | $R^5$ | $R^6$ | $R^7$ | physical data |
|---|---|---|---|---|---|---|---|---|---|---|
| 3.41 | $CO_2C_2H_5$ | H | $CH_3$ | $CH_3$ | $CH_3$ | H | H | H | H | |
| 3.42 | $CO_2C_2H_5$ | SH | $CH_3$ | $CH_3$ | $CH_3$ | H | H | H | H | |
| 3.43 | $CO_2C_2H_5$ | H | $CH_3$ | $CH_3$ | $CH_3$ | H | H | 6-$OCH_3$ | H | |
| 3.44 | $CO_2C_2H_5$ | H | $CH_3$ | $CH_3$ | $CH_3$ | H | H | 6-$OCH_3$ | 7-$OCH_3$ | |
| 3.45 | $CO_2C_2H_5$ | H | $C_2H_5$ | H | H | H | H | H | H | |
| 3.46 | $CO_2C_2H_5$ | H | $C_2H_5$ | H | $CH_3$ | H | H | H | H | |
| 3.47 | $CO_2C_2H_5$ | H | $C_2H_5$ | $C_2H_5$ | H | H | H | H | H | |
| 3.48 | $CO_2C_2H_5$ | H | $C_2H_5$ | $C_2H_5$ | $CH_3$ | H | H | H | H | |
| 3.49 | $CO_2C_2H_5$ | SH | $C_2H_5$ | $C_2H_5$ | $CH_3$ | H | H | H | H | |
| 3.50 | $CO_2C_2H_5$ | H | —$CH_2$—$CH_2$— | | $CH_3$ | H | H | H | H | |
| 3.51 | $COCH_3$ | H | H | H | H | H | H | H | H | |
| 3.52 | $COCH_3$ | SH | H | H | $CH_3$ | H | H | H | H | |
| 3.53 | $COCH_3$ | H | $CH_3$ | H | $CH_3$ | H | H | H | H | |
| 3.54 | $COCH_3$ | H | $CH_3$ | $CH_3$ | H | H | H | H | H | |
| 3.55 | $COCH_3$ | H | $CH_3$ | $CH_3$ | $CH_3$ | H | H | H | H | |
| 3.56 | $COCH_3$ | H | $CH_3$ | $CH_3$ | H | H | H | 6-$CH_3$ | H | |
| 3.57 | $COCH_3$ | H | $CH_3$ | $CH_3$ | H | H | H | 6-$OCH_3$ | H | |
| 3.58 | $COCH_3$ | H | $CH_3$ | $CH_3$ | $CH_3$ | H | H | 6-$OCH_3$ | H | |
| 3.59 | $COCH_3$ | H | $C_2H_5$ | $C_2H_5$ | H | H | H | H | H | |
| 3.60 | $COCH_3$ | H | $C_2H_5$ | $C_2H_5$ | $CH_3$ | H | H | H | H | |
| 3.61 | $CO_2C_2H_5$ | H | $CH_3$ | H | H | H | H | H | H | |
| 3.62 | $CO_2C_2H_5$ | H | $CH_3$ | H | $CH_3$ | H | H | H | H | |
| 3.63 | $CO_2C_2H_5$ | H | $CH_3$ | $CH_3$ | H | H | H | H | H | |
| 3.64 | $CO_2C_2H_5$ | H | $CH_3$ | $CH_3$ | $CH_3$ | H | H | H | H | |
| 3.65 | $CO_2C_2H_5$ | H | $C_2H_5$ | $C_2H_5$ | $CH_3$ | H | H | H | H | |
| 3.66 | $CO_2C_2H_5$ | H | $C_2H_5$ | $C_2H_5$ | H | H | H | H | H | |
| 3.67 | $CONH_2$ | H | $CH_3$ | H | H | H | H | H | H | |
| 3.68 | $CONH_2$ | H | $CH_3$ | H | $CH_3$ | H | H | H | H | |
| 3.69 | $CONH_2$ | H | $CH_3$ | $CH_3$ | H | H | H | H | H | |
| 3.70 | $CONH_2$ | H | $CH_3$ | $CH_3$ | $CH_3$ | H | H | H | H | |
| 3.71 | $CONH_2$ | H | $C_2H_5$ | $C_2H_5$ | H | H | H | H | H | |
| 3.72 | $CONH_2$ | H | $C_2H_5$ | $C_2H_5$ | $CH_3$ | H | H | H | H | |
| 3.73 | $CONHCH_3$ | H | $CH_3$ | H | H | H | H | H | H | |
| 3.74 | $CONHCH_3$ | H | $CH_3$ | H | $CH_3$ | H | H | H | H | |
| 3.75 | $CONHCH_3$ | H | $CH_3$ | $CH_3$ | H | H | H | H | H | |
| 3.76 | $CONHCH_3$ | H | $CH_3$ | $CH_3$ | $CH_3$ | H | H | H | H | |
| 3.77 | $CONHCH_3$ | H | $C_2H_5$ | $C_2H_5$ | H | H | H | H | H | |
| 3.78 | $CONHCH_3$ | H | $C_2H_5$ | $C_2H_5$ | $CH_3$ | H | H | H | H | |
| 3.79 | $CONHCH_3$ | H | —$CH_2$—$CH_2$— | | H | H | H | H | H | |
| 3.80 | $CONHCH_3$ | H | —$CH_2$—$CH_2$— | | $CH_3$ | H | H | H | H | |
| 3.81 | $CON(CH_3)_2$ | H | $CH_3$ | $CH_3$ | H | H | H | H | H | |
| 3.82 | $CON(CH_3)_2$ | H | $CH_3$ | $CH_3$ | $CH_3$ | H | H | H | H | |
| 3.83 | $CON(CH_3)_2$ | H | $C_2H_5$ | $C_2H_5$ | H | H | H | H | H | |
| 3.84 | $CON(CH_3)_2$ | H | $C_2H_5$ | $C_2H_5$ | $CH_3$ | H | H | H | H | |
| 3.85 | CN | H | $CH_3$ | $CH_3$ | H | H | H | H | H | |
| 3.86 | CN | H | $CH_3$ | $CH_3$ | $CH_3$ | H | H | H | H | |

TABLE 4

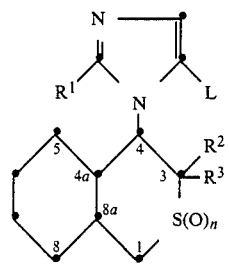

| Comp. No. | L | R¹ | R² | R³ | n | Pos. 4a-8a | Pos. 4-4a | physical data |
|---|---|---|---|---|---|---|---|---|
| 4.01 | CO$_2$CH$_3$ | H | H | H | 0 | — | — | |
| 4.02 | CO$_2$CH$_3$ | H | H | H | 0 | trans | trans | |
| 4.03 | CO$_2$CH$_3$ | H | H | H | 0 | trans | cis | m.p. 157–158° C. |
| 4.04 | CO$_2$CH$_3$ | SH | H | H | 0 | — | — | |
| 4.05 | CO$_2$CH$_3$ | H | CH$_3$ | H | 0 | — | — | |
| 4.06 | CO$_2$CH$_3$ | H | CH$_3$ | H | 0 | trans | trans | |
| 4.07 | CO$_2$CH$_3$ | H | CH$_3$ | H | 0 | trans | trans | |
| 4.08 | CO$_2$CH$_3$ | SH | CH$_3$ | H | 0 | — | — | |
| 4.09 | CO$_2$CH$_3$ | H | CH$_3$ | CH$_3$ | 0 | — | — | |
| 4.10 | CO$_2$CH$_3$ | H | CH$_3$ | CH$_3$ | 0 | trans | trans | |
| 4.11 | CO$_2$CH$_3$ | H | CH$_3$ | CH$_3$ | 0 | trans | trans | |
| 4.12 | CO$_2$CH$_3$ | H | C$_2$H$_5$ | H | 0 | — | — | |
| 4.13 | CO$_2$CH$_3$ | H | C$_2$H$_5$ | C$_2$H$_5$ | 0 | — | — | |
| 4.14 | CO$_2$CH$_3$ | H | C$_2$H$_5$ | C$_2$H$_5$ | 0 | trans | cis | |
| 4.15 | CO$_2$CH$_3$ | H | C$_2$H$_5$ | C$_2$H$_5$ | 0 | trans | trans | |
| 4.16 | CO$_2$CH$_3$ | H | —CH$_2$—CH$_2$— | | 0 | — | — | |
| 4.17 | CO$_2$CH$_3$ | H | C$_2$H$_5$ | CH$_3$ | 0 | — | — | |
| 4.18 | CO$_2$C$_2$H$_5$ | H | H | H | 0 | — | — | |
| 4.19 | CO$_2$C$_2$H$_5$ | H | CH$_3$ | H | 0 | — | — | |
| 4.20 | CO$_2$C$_2$H$_5$ | H | CH$_3$ | CH$_3$ | 0 | — | — | |
| 4.21 | CO$_2$C$_2$H$_5$ | H | CH$_3$ | CH$_3$ | 0 | trans | — | |
| 4.22 | CO$_2$C$_2$H$_5$ | H | C$_2$H$_5$ | H | 0 | — | — | |
| 4.23 | CO$_2$C$_2$H$_5$ | H | C$_2$H$_5$ | C$_2$H$_5$ | 0 | — | — | |
| 4.24 | CO$_2$C$_2$H$_5$ | H | C$_2$H$_5$ | C$_2$H$_5$ | 0 | trans | — | |
| 4.25 | CO$_2$C$_2$H$_5$ | H | —CH$_2$—CH$_2$— | | 0 | — | — | |
| 4.26 | CO$_2$C$_2$H$_5$ | H | C$_2$H$_5$ | CH$_3$ | 0 | — | — | |
| 4.27 | CONH$_2$ | H | CH$_3$ | H | 0 | — | — | |
| 4.28 | CONH$_2$ | H | CH$_3$ | CH$_3$ | 0 | — | — | |
| 4.29 | CONH$_2$ | H | C$_2$H$_5$ | H | 0 | — | — | |
| 4.30 | CONH$_2$ | H | C$_2$H$_5$ | C$_2$H$_5$ | 0 | — | — | |
| 4.31 | CONHCH$_3$ | H | H | H | 0 | — | — | |
| 4.32 | CONHCH$_3$ | H | CH$_3$ | H | 0 | — | — | |
| 4.33 | CONHCH$_3$ | H | CH$_3$ | CH$_3$ | 0 | — | — | |
| 4.34 | CONHCH$_3$ | H | C$_2$H$_5$ | H | 0 | — | — | |
| 4.35 | CONHCH$_3$ | H | C$_2$H$_5$ | C$_2$H$_5$ | 0 | — | — | |
| 4.36 | CON(CH$_3$)$_2$ | H | H | H | 0 | — | — | |
| 4.37 | CON(CH$_3$)$_2$ | H | CH$_3$ | H | 0 | — | — | |
| 4.38 | CON(CH$_3$)$_2$ | H | CH$_3$ | CH$_3$ | 0 | — | — | |
| 4.39 | CON(CH$_3$)$_2$ | H | C$_2$H$_5$ | C$_2$H$_5$ | 0 | — | — | |
| 4.40 | COCH$_3$ | H | H | H | 0 | — | — | |
| 4.41 | COCH$_3$ | H | CH$_3$ | CH$_3$ | 0 | — | — | |
| 4.42 | COCH$_3$ | H | C$_2$H$_5$ | C$_2$H$_5$ | 0 | — | — | |
| 4.43 | COC$_2$H$_5$ | H | H | H | 0 | — | — | |
| 4.44 | COC$_2$H$_5$ | H | CH$_3$ | CH$_3$ | 0 | — | — | |
| 4.45 | CO$_2$CH$_2$CH=CH$_2$ | H | H | H | 0 | — | — | |
| 4.46 | CO$_2$CH$_2$C≡CH | H | H | H | 0 | — | — | |
| 4.47 | CO$_2$CH$_3$ | H | H | H | 1 | — | — | |
| 4.48 | CO$_2$CH$_3$ | H | CH$_3$ | H | 1 | — | — | |
| 4.49 | CO$_2$CH$_3$ | H | CH$_3$ | CH$_3$ | 1 | — | — | |
| 4.50 | CO$_2$CH$_3$ | H | C$_2$H$_5$ | C$_2$H$_5$ | 1 | — | — | |
| 4.51 | CO$_2$C$_2$H$_5$ | H | H | H | 1 | — | — | |
| 4.52 | CO$_2$C$_2$H$_5$ | H | CH$_3$ | CH$_3$ | 1 | — | — | |
| 4.53 | CO$_2$C$_2$H$_5$ | H | C$_2$H$_5$ | C$_2$H$_5$ | 1 | — | — | |
| 4.54 | COCH$_3$ | H | CH$_3$ | H | 1 | — | — | |
| 4.55 | COCH$_3$ | H | CH$_3$ | CH$_3$ | 1 | — | — | |
| 4.56 | COCH$_3$ | H | C$_2$H$_5$ | C$_2$H$_5$ | 1 | — | — | |
| 4.57 | CO$_2$C$_2$H$_5$ | H | CH$_3$ | CH$_3$ | 1 | — | — | |
| 4.58 | CONH$_2$ | H | CH$_3$ | CH$_3$ | 1 | — | — | |
| 4.59 | CONHCH$_3$ | H | CH$_3$ | CH$_3$ | 1 | — | — | |
| 4.60 | CON(CH$_3$)$_2$ | H | CH$_3$ | CH$_3$ | 1 | — | — | |
| 4.61 | CN | H | CH$_3$ | CH$_3$ | 1 | — | — | |
| 4.62 | CO$_2$CH$_3$ | H | H | H | 2 | — | — | |
| 4.63 | CO$_2$CH$_3$ | H | CH$_3$ | CH$_3$ | 2 | — | — | |
| 4.64 | CO$_2$C$_2$H$_5$ | H | CH$_3$ | CH$_3$ | 2 | — | — | |
| 4.65 | COCH$_3$ | H | CH$_3$ | CH$_3$ | 2 | — | — | |
| 4.66 | COC$_2$H$_5$ | H | CH$_3$ | CH$_3$ | 2 | — | — | |

TABLE 4-continued

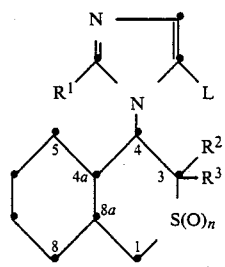

| Comp. No. | L | R¹ | R² | R³ | n | Pos. 4a-8a | Pos. 4-4a | physical data |
|---|---|---|---|---|---|---|---|---|
| 4.67 | CONH₂ | H | CH₃ | CH₃ | 2 | — | — | |
| 4.68 | CONHCH₃ | H | CH₃ | CH₃ | 2 | — | — | |
| 4.69 | CON(CH₃)₂ | H | CH₃ | CH₃ | 2 | — | — | |
| 4.70 | CN | H | CH₃ | CH₃ | 2 | — | — | |

TABLE 5

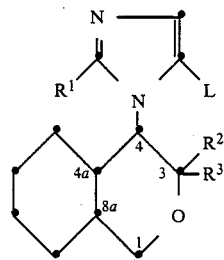

| Comp. No. | L | R¹ | R² | R³ | Pos. 4a-8a | Pos. 4-4a | physical data |
|---|---|---|---|---|---|---|---|
| 5.01 | CO₂CH₃ | H | H | H | — | — | |
| 5.02 | CO₂CH₃ | H | H | H | trans | trans | |
| 5.03 | CO₂CH₃ | H | H | H | trans | cis | |
| 5.04 | CO₂CH₃ | SH | H | H | — | — | |
| 5.05 | CO₂CH₃ | H | CH₃ | H | — | — | |
| 5.06 | CO₂CH₃ | H | CH₃ | H | trans | trans | |
| 5.07 | CO₂CH₃ | H | CH₃ | H | trans | trans | |
| 5.08 | CO₂CH₃ | SH | CH₃ | H | — | — | |
| 5.09 | CO₂CH₃ | H | CH₃ | CH₃ | — | — | |
| 5.10 | CO₂CH₃ | H | CH₃ | CH₃ | trans | trans | |
| 5.11 | CO₂CH₃ | H | CH₃ | CH₃ | trans | trans | |
| 5.12 | CO₂CH₃ | H | C₂H₅ | H | — | — | |
| 5.13 | CO₂CH₃ | H | C₂H₅ | C₂H₅ | — | — | |
| 5.14 | CO₂CH₃ | H | C₂H₅ | C₂H₅ | trans | cis | |
| 5.15 | CO₂CH₃ | H | C₂H₅ | C₂H₅ | trans | trans | |
| 5.16 | CO₂CH₃ | H | —CH₂—CH₂— | | — | — | |
| 5.17 | CO₂CH₃ | H | C₂H₅ | CH₃ | — | — | |
| 5.18 | CO₂C₂H₅ | H | H | H | — | — | |
| 5.19 | CO₂C₂H₅ | H | CH₃ | H | — | — | |
| 5.20 | CO₂C₂H₅ | H | CH₃ | CH₃ | — | — | |
| 5.21 | CO₂C₂H₅ | H | CH₃ | CH₃ | trans | — | |
| 5.22 | CO₂C₂H₅ | H | C₂H₅ | H | — | — | |
| 5.23 | CO₂C₂H₅ | H | C₂H₅ | C₂H₅ | — | — | |
| 5.24 | CO₂C₂H₅ | H | C₂H₅ | C₂H₅ | trans | — | |
| 5.25 | CO₂C₂H₅ | H | —CH₂—CH₂— | | — | — | |
| 5.26 | CO₂C₂H₅ | H | C₂H₅ | CH₃ | — | — | |
| 5.27 | CONH₂ | H | CH₃ | H | — | — | |
| 5.28 | CONH₂ | H | CH₃ | CH₃ | — | — | |
| 5.29 | CONH₂ | H | C₂H₅ | H | — | — | |
| 5.30 | CONH₂ | H | C₂H₅ | C₂H₅ | — | — | |
| 5.31 | CONHCH₃ | H | H | H | — | — | |
| 5.32 | CONHCH₃ | H | CH₃ | H | — | — | |
| 5.33 | CONHCH₃ | H | CH₃ | CH₃ | — | — | |
| 5.34 | CONHCH₃ | H | C₂H₅ | H | — | — | |
| 5.35 | CONHCH₃ | H | C₂H₅ | C₂H₅ | — | — | |
| 5.36 | CON(CH₃)₂ | H | H | H | — | — | |
| 5.37 | CON(CH₃)₂ | H | CH₃ | H | — | — | |
| 5.38 | CON(CH₃)₂ | H | CH₃ | CH₃ | — | — | |
| 5.39 | CON(CH₃)₂ | H | C₂H₅ | C₂H₅ | — | — | |
| 5.40 | COCH₃ | H | H | H | — | — | |
| 5.41 | COCH₃ | H | CH₃ | CH₃ | — | — | |
| 5.42 | COCH₃ | H | C₂H₅ | C₂H₅ | — | — | |

TABLE 5-continued

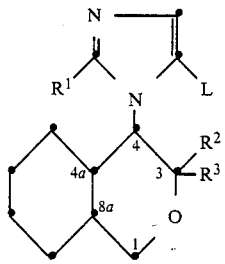

| Comp. No. | L | R¹ | R² | R³ | Pos. 4a–8a | Pos. 4–4a | physical data |
|---|---|---|---|---|---|---|---|
| 5.43 | $COC_2H_5$ | H | H | H | — | — | |
| 5.44 | $COC_2H_5$ | H | $CH_3$ | $CH_3$ | — | — | |
| 5.45 | $CO_2CH_2CH=CH_2$ | H | H | H | — | — | |
| 5.46 | $CO_2CH_2C\equiv CH$ | H | H | H | — | — | |

TABLE 6

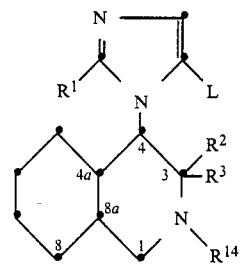

| Comp. No. | L | R¹ | R² | R³ | R¹⁴ | physical data |
|---|---|---|---|---|---|---|
| 6.01 | $CO_2CH_3$ | H | H | H | H | |
| 6.02 | $CO_2CH_3$ | H | H | H | $CH_3$ | |
| 6.03 | $CO_2CH_3$ | H | H | H | Benzyl | |
| 6.04 | $CO_2CH_3$ | H | $CH_3$ | H | H | |
| 6.05 | $CO_2CH_3$ | H | $CH_3$ | H | $CH_3$ | |
| 6.06 | $CO_2CH_3$ | H | $CH_3$ | $CH_3$ | H | |
| 6.07 | $CO_2CH_3$ | H | $CH_3$ | $CH_3$ | $CH_3$ | |
| 6.08 | $CO_2CH_3$ | H | $C_2H_5$ | H | H | |
| 6.09 | $CO_2CH_3$ | H | $C_2H_5$ | H | $CH_3$ | |
| 6.10 | $CO_2CH_3$ | H | $C_2H_5$ | $C_2H_5$ | H | |
| 6.11 | $CO_2CH_3$ | H | $C_2H_5$ | $C_2H_5$ | $CH_3$ | |
| 6.12 | $CO_2CH_3$ | H | $C_3H_7$—i | H | H | |
| 6.13 | $CO_2CH_3$ | H | $C_3H_7$—i | H | $CH_3$ | |
| 6.14 | $CO_2CH_3$ | H | $C_4H_9$—i | H | H | |
| 6.15 | $CO_2CH_3$ | H | $C_4H_9$—i | H | $CH_3$ | |
| 6.16 | $CO_2C_2H_5$ | H | $CH_3$ | H | H | |
| 6.17 | $CO_2C_2H_5$ | H | $CH_3$ | H | $CH_3$ | |
| 6.18 | $CO_2C_2H_5$ | H | $CH_3$ | $CH_3$ | $CH_3$ | |
| 6.19 | $CO_2C_2H_5$ | H | $C_2H_5$ | H | $CH_3$ | |
| 6.20 | $CO_2C_2H_5$ | H | $C_2H_5$ | $C_2H_5$ | $CH_3$ | |
| 6.21 | $CO_2C_2H_5$ | H | $C_3H_7$—i | H | $CH_3$ | |
| 6.22 | $COCH_3$ | H | $CH_3$ | $CH_3$ | H | |

TABLE 6-continued

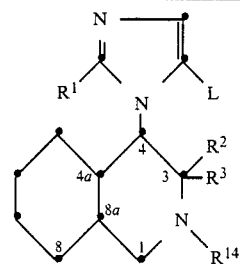

| Comp. No. | L | R¹ | R² | R³ | R¹⁴ | physical data |
|---|---|---|---|---|---|---|
| 6.23 | $COCH_3$ | H | $CH_3$ | $CH_3$ | $CH_3$ | |
| 6.24 | $COCH_3$ | H | $C_2H_5$ | H | $CH_3$ | |
| 6.25 | $COCH_3$ | H | $C_2H_5$ | $C_2H_5$ | $CH_3$ | |
| 6.26 | $COCH_3$ | H | $C_2H_5$ | $C_2H_5$ | H | |
| 6.27 | $COC_2H_5$ | H | $CH_3$ | $CH_3$ | H | |
| 6.28 | $COC_2H_5$ | H | $CH_3$ | $CH_3$ | $CH_3$ | |
| 6.29 | $COC_2H_5$ | H | $C_2H_5$ | H | $CH_3$ | |
| 6.30 | $COC_2H_5$ | H | $C_2H_5$ | $C_2H_5$ | $CH_3$ | |
| 6.31 | $COC_2H_5$ | H | $C_2H_5$ | $C_2H_5$ | H | |
| 6.32 | $CONH_2$ | H | $CH_3$ | $CH_3$ | H | |
| 6.33 | $CONH_2$ | H | $CH_3$ | $CH_3$ | $CH_3$ | |
| 6.34 | $CONH_2$ | H | $C_2H_5$ | $C_2H_5$ | H | |
| 6.35 | $CONHCH_3$ | H | $CH_3$ | $CH_3$ | H | |
| 6.36 | $CON(CH_3)_2$ | H | $CH_3$ | $CH_3$ | $CH_3$ | |
| 6.37 | $CON(CH_3)_2$ | H | $CH_3$ | $CH_3$ | H | |
| 6.38 | $CON(CH_3)_2$ | H | $CH_3$ | $CH_3$ | $CH_3$ | |
| 6.39 | $CO_2CH_2CH=CH_2$ | H | $CH_3$ | $CH_3$ | H | |
| 6.40 | $CO_2CH_2CH=CH_2$ | H | $CH_3$ | $CH_3$ | $CH_3$ | |
| 6.41 | $CO_2CH_2C\equiv CH$ | H | $CH_3$ | $CH_3$ | H | |
| 6.42 | $CO_2CH_2C\equiv CH$ | H | $CH_3$ | $CH_3$ | $CH_3$ | |
| 6.43 | CN | H | $CH_3$ | $CH_3$ | H | |
| 6.44 | CN | H | $CH_3$ | $CH_3$ | $CH_3$ | |

TABLE 7

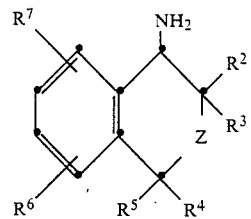

| Comp. No. | R² | R³ | Z | R⁴ | R⁵ | R⁶ | R⁷ | physical data |
|---|---|---|---|---|---|---|---|---|
| 7.01 | H | H | S | H | H | H | H | $b.p._{0.06} = 80°$ C. |

TABLE 7-continued

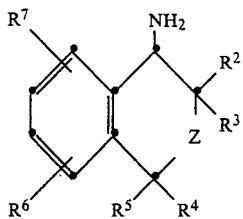

| Comp. No. | R² | R³ | Z | R⁴ | R⁵ | R⁶ | R⁷ | physical data |
|---|---|---|---|---|---|---|---|---|
| 7.02 | H | H | S | CH₃ | H | H | H | |
| 7.03 | CH₃ | H | S | H | H | H | H | |
| 7.04 | CH₃ | CH₃ | S | H | H | H | H | b.p.₀,₀₆ = 80° C. |
| 7.05 | CH₃ | CH₃ | S | CH₃ | H | H | H | |
| 7.06 | CH₃ | CH₃ | S | H | H | 7-OCH₃ | H | |
| 7.07 | CH₃ | CH₃ | S | CH₃ | H | 6-CH₃ | H | |
| 7.08 | CH₃ | CH₃ | S | H | H | 5-CH₃ | 8-CH₃ | |
| 7.09 | —CH₂—CH₂— | | S | H | H | H | H | |
| 7.10 | H | H | S | C₂H₅ | H | H | H | |
| 7.11 | C₂H₅ | H | S | H | H | H | H | b.p.₀,₀₄ = 90° C. |
| 7.12 | C₂H₅ | C₂H₅ | S | H | H | H | H | |
| 7.13 | C₂H₅ | C₂H₅ | S | CH₃ | H | H | H | |
| 7.14 | C₂H₅ | C₂H₅ | S | H | H | 6-CH₃ | H | |
| 7.15 | H | H | O | H | H | H | H | |
| 7.16 | H | H | O | CH₃ | H | H | H | |
| 7.17 | CH₃ | H | O | H | H | H | H | |
| 7.18 | CH₃ | CH₃ | O | H | H | H | H | |
| 7.19 | CH₃ | CH₃ | O | CH₃ | H | H | H | |
| 7.20 | CH₃ | CH₃ | O | H | H | 7-OCH₃ | H | |
| 7.21 | CH₃ | CH₃ | O | CH₃ | H | 6-CH₃ | H | |
| 7.22 | CH₃ | CH₃ | O | H | H | 5-CH₃ | 8-CH₃ | |
| 7.23 | —CH₂—CH₂— | | O | H | H | H | H | |
| 7.24 | H | H | O | C₂H₅ | H | H | H | |
| 7.25 | C₂H₅ | H | O | H | H | H | H | |
| 7.26 | C₂H₅ | C₂H₅ | O | H | H | H | H | |
| 7.27 | C₂H₅ | C₂H₅ | O | CH₃ | H | H | H | |
| 7.28 | C₂H₅ | C₂H₅ | O | H | H | 6-CH₃ | H | |
| 7.29 | CH₃ | H | NCH₃ | H | H | H | H | |
| 7.30 | CH₃ | H | NCH₃ | H | H | H | | |
| 7.31 | CH₃ | CH₃ | NCH₃ | H | H | H | H | |
| 7.32 | CH₃ | CH₃ | NH | H | H | H | H | |
| 7.33 | CH₃ | CH₃ | NH | H | H | 6-OCH₃ | 7-OCH₃ | |
| 7.34 | C₂H₅ | H | NCH₃ | H | H | H | H | |
| 7.35 | C₂H₅ | C₂H₅ | NH | H | H | H | H | |
| 7.36 | C₂H₅ | C₂H₅ | NCH₃ | H | H | H | H | |
| 7.37 | H | H | SO | H | H | H | H | |
| 7.38 | H | H | SO | CH₃ | H | H | H | |
| 7.39 | CH₃ | H | SO | H | H | H | H | |
| 7.40 | CH₃ | CH₃ | SO | H | H | H | H | |
| 7.41 | CH₃ | CH₃ | SO | CH₃ | H | H | H | |
| 7.42 | CH₃ | CH₃ | SO | H | H | 7-OCH₃ | H | |
| 7.43 | CH₃ | CH₃ | SO | CH₃ | H | 6-CH₃ | H | |
| 7.44 | CH₃ | CH₃ | SO | H | H | 5-CH₃ | 8-CH₃ | |
| 7.45 | —CH₂—CH₂— | | SO | H | H | H | H | |
| 7.46 | H | H | SO | C₂H₅ | H | H | H | |
| 7.47 | C₂H₅ | H | SO | H | H | H | H | |
| 7.48 | C₂H₅ | C₂H₅ | SO | H | H | H | H | |
| 7.49 | C₂H₅ | C₂H₅ | SO | CH₃ | H | H | H | |
| 7.50 | C₂H₅ | C₂H₅ | SO₂ | H | H | 6-CH₃ | H | |
| 7.51 | H | H | SO₂ | H | H | H | H | |
| 7.52 | H | H | SO₂ | CH₃ | H | H | H | |
| 7.53 | CH₃ | H | SO₂ | H | H | H | H | |
| 7.54 | CH₃ | CH₃ | SO₂ | H | H | H | H | |
| 7.55 | CH₃ | CH₃ | SO₂ | CH₃ | H | H | H | |
| 7.56 | CH₃ | CH₃ | SO₂ | H | H | 7-OCH₃ | H | |
| 7.57 | CH₃ | CH₃ | SO₂ | CH₃ | H | 6-CH₃ | H | |
| 7.58 | CH₃ | CH₃ | SO₂ | H | H | 5-CH₃ | 8-CH₃ | |
| 7.59 | —CH₂—CH₂— | | SO₂ | H | H | H | H | |
| 7.60 | H | H | SO₂ | C₂H₅ | H | H | H | |
| 7.61 | C₂H₅ | H | SO₂ | H | H | H | H | |
| 7.62 | C₂H₅ | C₂H₅ | SO₂ | H | H | H | H | |
| 7.63 | C₂H₅ | C₂H₅ | SO₂ | CH₃ | H | H | H | |
| 7.64 | C₂H₅ | C₂H₅ | SO₂ | H | H | 6-CH₃ | H | |

TABLE 8

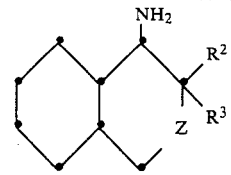

| Comp. No. | R² | R³ | Z | physical data |
|---|---|---|---|---|
| 8.01 | H | H | S | b.p.$_{0.02}$ = 60° C. |
| 8.02 | CH₃ | H | S | |
| 8.03 | CH₃ | CH₃ | S | |
| 8.04 | C₂H₅ | H | S | |
| 8.05 | C₂H₅ | C₂H₅ | S | |
| 8.06 | —CH₂—CH₂— | | S | |
| 8.07 | H | H | O | |
| 8.08 | CH₃ | H | O | |
| 8.09 | CH₃ | CH₃ | O | |
| 8.10 | C₂H₅ | H | O | |
| 8.11 | C₂H₅ | C₂H₅ | O | |

TABLE 8-continued

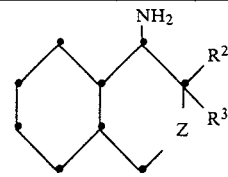

| Comp. No. | R² | R³ | Z | physical data |
|---|---|---|---|---|
| 8.12 | —CH₂—CH₂— | | O | |
| 8.13 | H | H | NH | |
| 8.14 | H | H | NCH₃ | |
| 8.15 | CH₃ | H | NCH₃ | |
| 8.16 | CH₃ | CH₃ | NH | |
| 8.17 | CH₃ | CH₃ | NCH₃ | |
| 8.18 | C₂H₅ | H | NH | |
| 8.19 | C₂H₅ | H | NCH₃ | |
| 8.20 | C₂H₅ | C₂H₅ | NH | |
| 8.21 | C₂H₅ | C₂H₅ | NCH₃ | |

TABLE 9

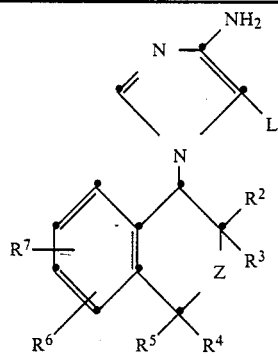

| Comp. No. | L | R² | R³ | Z | R⁴ | R⁵ | R⁶ | R⁷ | physical data |
|---|---|---|---|---|---|---|---|---|---|
| 9.01 | CO₂CH₃ | H | H | S | H | H | H | H | |
| 9.02 | CO₂CH₃ | CH₃ | H | S | H | H | H | H | |
| 9.03 | CO₂CH₃ | CH₃ | H | S | CH₃ | H | H | H | |
| 9.04 | CO₂CH₃ | CH₃ | H | S | CH₃ | H | 5-CH₃ | H | |
| 9.05 | CO₂CH₃ | CH₃ | H | S | CH₃ | H | 6-CH₃ | H | |
| 9.06 | CO₂CH₃ | CH₃ | H | S | CH₃ | H | 6-OCH₃ | H | |
| 9.07 | CO₂CH₃ | CH₃ | H | S | CH₃ | H | 5-CH₃ | 8-CH₃ | |
| 9.08 | CO₂CH₃ | CH₃ | CH₃ | S | H | H | H | H | |
| 9.09 | CO₂CH₃ | CH₃ | CH₃ | S | CH₃ | H | H | H | |
| 9.10 | CO₂CH₃ | CH₃ | CH₃ | S | H | H | 6-CH₃ | H | |
| 9.11 | CO₂CH₃ | CH₃ | CH₃ | S | H | H | 6-OCH₃ | H | |
| 9.12 | CO₂CH₃ | CH₃ | CH₃ | S | H | H | 6-NO₂ | H | |
| 9.13 | CO₂CH₃ | CH₃ | CH₃ | S | H | H | 5-F | H | |
| 9.14 | CO₂CH₃ | —CH₂—CH₂— | | S | H | H | H | H | |
| 9.15 | CO₂CH₃ | C₂H₅ | H | S | H | H | H | H | m.p. 149–150° C. |
| 9.16 | CO₂CH₃ | C₂H₅ | C₂H₅ | S | H | H | H | H | |
| 9.17 | CO₂CH₃ | C₂H₅ | C₂H₅ | S | H | H | 6-CH₃ | H | |
| 9.18 | CO₂CH₃ | C₂H₅ | C₂H₅ | S | CH₃ | H | H | H | |
| 9.19 | CO₂CH₃ | —(CH₂)₄— | | S | H | H | H | H | |
| 9.20 | CO₂C₂H₅ | H | H | S | H | H | H | H | |
| 9.21 | CO₂C₂H₅ | CH₃ | H | S | H | H | H | H | |
| 9.22 | CO₂C₂H₅ | CH₃ | CH₃ | S | H | H | H | H | |
| 9.23 | CO₂C₂H₅ | CH₃ | CH₃ | S | H | H | 6-OCH₃ | H | |
| 9.24 | CO₂C₂H₅ | C₂H₅ | C₂H₅ | S | H | H | H | H | |
| 9.25 | CO₂C₂H₅ | C₂H₅ | H | S | H | H | H | H | |
| 9.26 | CO₂C₂H₅ | —CH₂—CH₂— | | S | H | H | H | H | |
| 9.27 | COCH₃ | CH₃ | H | S | H | H | H | H | |
| 9.28 | COCH₃ | CH₃ | CH₃ | S | H | H | H | H | |
| 9.29 | COC₂H₅ | CH₃ | CH₃ | S | H | H | H | H | |
| 9.30 | CON(CH₃)₂ | CH₃ | CH₃ | S | H | H | H | H | |
| 9.31 | CO₂CH₃ | CH₃ | H | SO | H | H | H | H | |
| 9.32 | CO₂CH₃ | CH₃ | CH₃ | SO | H | H | H | H | |
| 9.33 | CO₂CH₃ | C₂H₅ | H | SO | H | H | H | H | |
| 9.34 | CO₂CH₃ | C₂H₅ | C₂H₅ | SO | H | H | H | H | |
| 9.35 | CO₂C₂H₅ | CH₃ | H | SO | H | H | H | H | |
| 9.36 | CO₂C₂H₅ | CH₃ | CH₃ | SO | H | H | H | H | |

TABLE 9-continued

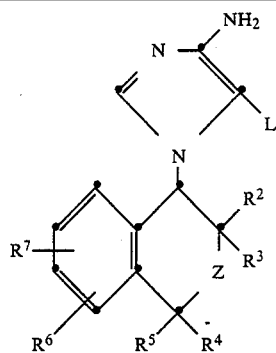

| Comp. No. | L | R² | R³ | Z | R⁴ | R⁵ | R⁶ | R⁷ | physical data |
|---|---|---|---|---|---|---|---|---|---|
| 9.37 | CO₂C₂H₅ | C₂H₅ | C₂H₅ | SO | H | H | H | H | |
| 9.38 | COCH₃ | CH₃ | CH₃ | SO | H | H | H | H | |
| 9.39 | CO₂C₂H₅ | CH₃ | CH₃ | SO | H | H | H | H | |
| 9.40 | CON(CH₃)₂ | CH₃ | CH₃ | SO | H | H | H | H | |
| 9.41 | CO₂CH₃ | CH₃ | H | SO₂ | H | H | H | H | |
| 9.42 | CO₂CH₃ | CH₃ | CH₃ | SO₂ | H | H | H | H | |
| 9.43 | CO₂CH₃ | C₂H₅ | H | SO₂ | H | H | H | H | |
| 9.44 | CO₂CH₃ | C₂H₅ | C₂H₅ | SO₂ | H | H | H | H | |
| 9.45 | CO₂CH₃ | —CH₂—CH₂— | | SO₂ | H | H | H | H | |
| 9.46 | CO₂C₂H₅ | CH₃ | H | SO₂ | H | H | H | H | |
| 9.47 | CO₂C₂H₅ | CH₃ | CH₃ | SO₂ | H | H | H | H | |
| 9.48 | CO₂C₂H₅ | C₂H₅ | C₂H₅ | SO₂ | H | H | H | H | |
| 9.49 | COCH₃ | CH₃ | CH₃ | SO₂ | H | H | H | H | |
| 9.50 | CO₂C₂H₅ | CH₃ | CH₃ | SO₂ | H | H | H | H | |
| 9.51 | CON(CH₃)₂ | CH₃ | CH₃ | SO₂ | H | H | H | H | |
| 9.52 | CO₂CH₃ | H | H | O | H | H | H | H | |
| 9.53 | CO₂CH₃ | CH₃ | H | O | H | H | H | H | |
| 9.54 | CO₂CH₃ | CH₃ | CH₃ | O | H | H | H | H | |
| 9.55 | CO₂CH₃ | C₂H₅ | H | O | H | H | H | H | |
| 9.56 | CO₂CH₃ | C₂H₅ | C₂H₅ | O | H | H | H | H | |
| 9.57 | CO₂CH₃ | —CH₂—CH₂— | | O | H | H | H | H | |
| 9.58 | CO₂C₂H₅ | CH₃ | H | O | H | H | H | H | |
| 9.59 | CO₂C₂H₅ | CH₃ | CH₃ | O | H | H | H | H | |
| 9.60 | CO₂C₂H₅ | C₂H₅ | C₂H₅ | O | H | H | H | H | |
| 9.61 | COCH₃ | CH₃ | H | O | H | H | H | H | |
| 9.62 | COCH₃ | CH₃ | CH₃ | O | H | H | H | H | |
| 9.63 | COCH₃ | C₂H₅ | H | O | H | H | H | H | |
| 9.64 | COCH₃ | C₂H₅ | C₂H₅ | O | H | H | H | H | |
| 9.65 | CO₂C₂H₅ | CH₃ | CH₃ | O | H | H | H | H | |
| 9.66 | CO₂C₂H₅ | C₂H₅ | C₂H₅ | O | H | H | H | H | |
| 9.67 | CON(CH₃)₂ | CH₃ | CH₃ | O | H | H | H | H | |
| 9.68 | CO₂CH₃ | H | H | NCH₃ | H | H | H | H | |
| 9.69 | CO₂CH₃ | CH₃ | H | NCH₃ | H | H | H | H | |
| 9.70 | CO₂CH₃ | CH₃ | CH₃ | NCH₃ | H | H | H | H | |
| 9.71 | CO₂CH₃ | C₂H₅ | H | NCH₃ | H | H | H | H | |
| 9.72 | CO₂CH₃ | C₂H₅ | C₂H₅ | NCH₃ | H | H | H | H | |
| 9.73 | CO₂C₂H₅ | CH₃ | CH₃ | NCH₃ | H | H | H | H | |
| 9.74 | CO₂C₂H₅ | C₂H₅ | C₂H₅ | NCH₃ | H | H | H | H | |
| 9.75 | COCH₃ | CH₃ | H | NCH₃ | H | H | H | H | |
| 9.76 | COCH₃ | CH₃ | CH₃ | NCH₃ | H | H | H | H | |
| 9.77 | COCH₃ | C₂H₅ | H | NCH₃ | H | H | H | H | |
| 9.78 | COCH₃ | C₂H₅ | C₂H₅ | NCH₃ | H | H | H | H | |
| 9.79 | COC₂H₅ | CH₃ | H | NCH₃ | H | H | H | H | |
| 9.80 | COC₂H₅ | CH₃ | CH₃ | NCH₃ | H | H | H | H | |

TABLE 10

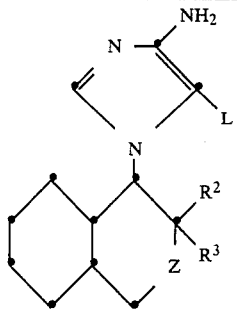

| Comp. No. | L | R² | R³ | Z | physical data |
|---|---|---|---|---|---|
| 10.01 | CO₂CH₃ | H | H | S | |
| 10.02 | CO₂CH₃ | CH₃ | H | S | |
| 10.03 | CO₂CH₃ | CH₃ | CH₃ | S | |
| 10.04 | CO₂CH₃ | C₂H₅ | H | S | |
| 10.05 | CO₂CH₃ | C₂H₅ | C₂H₅ | S | |
| 10.06 | CO₂C₂H₅ | CH₃ | CH₃ | S | |
| 10.07 | CO₂C₂H₅ | C₂H₅ | H | S | |
| 10.08 | CO₂C₂H₅ | C₂H₅ | C₂H₅ | S | |
| 10.09 | COCH₃ | CH₃ | CH₃ | S | |
| 10.10 | CON(CH₃)₂ | CH₃ | CH₃ | S | |
| 10.11 | CO₂CH₃ | H | H | SO | |
| 10.12 | CO₂CH₃ | CH₃ | CH₃ | SO | |
| 10.13 | CO₂C₂H₅ | CH₃ | CH₃ | SO | |
| 10.14 | COCH₃ | CH₃ | CH₃ | SO | |
| 10.15 | CO₂CH₃ | H | H | SO₂ | |
| 10.16 | CO₂CH₃ | CH₃ | CH₃ | SO₂ | |
| 10.17 | CO₂C₂H₅ | CH₃ | CH₃ | SO₂ | |
| 10.18 | COCH₃ | CH₃ | CH₃ | SO₂ | |
| 10.19 | CO₂CH₃ | H | H | O | |
| 10.20 | CO₂CH₃ | CH₃ | H | O | |
| 10.21 | CO₂CH₃ | CH₃ | CH₃ | O | |
| 10.22 | CO₂C₂H₅ | C₂H₅ | H | O | |
| 10.23 | CO₂C₂H₅ | C₂H₅ | C₂H₅ | O | |
| 10.24 | COCH₃ | CH₃ | CH₃ | O | |
| 10.25 | CO₂CH₃ | H | H | NCH₃ | |
| 10.26 | CO₂CH₃ | CH₃ | H | NCH₃ | |
| 10.27 | CO₂CH₃ | CH₃ | CH₃ | NCH₃ | |

FORMULATION EXAMPLES

Example F1: Formulation Examples for liquid active ingredients of formula I (throughout, percentages are by weight)

| (a) Emulsifiable concentrates | (a) | (b) | (c) |
|---|---|---|---|
| active ingredient of formula I | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any desired concentration can be produced from such concentrates by dilution with water.

| (b) Solutions | (a) | (b) | (c) | (d) |
|---|---|---|---|---|
| active ingredient of formula I | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| (c) Granulates | (a) | (b) |
|---|---|---|
| active ingredient of formula I | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| active ingredient of formula I | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Example F2: Formulation Examples for solid active ingredients of formula I (throughout, percentages are by weight)

| (a) Wettable powders | (a) | (b) |
|---|---|---|
| active ingredient No. 1.016 | 20% | 60% |
| sodium lignosulfonate | 5% | 5% |
| sodium laurylsulfate | 3% | — |
| sodium diisobutylnaphthalene-sulfonate | — | 6% |
| octylphenol polyethylene glycol ether (7–8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | |
|---|---|
| active ingredient No. 1.016 | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| (c) Dusts | (a) | (b) |
|---|---|---|
| active ingredient No. 1.016 | 5% | 8% |
| talcum | 95% | — |
| kaolin | — | 92% |

Ready-for-use dusts are obtained by mixing the active ingredient with the carrier and grinding the mixture in a suitable mill.

| (d) Extruder granulate | |
|---|---|
| active ingredient No. 2.034 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| (e) Coated granulate | |
|---|---|
| active ingredient No. 2.034 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | |
|---|---|
| active ingredient No. 1.016 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

Example B1: Pre-emergence herbicidal action

In a greenhouse, immediately after the test plants have been sown in seed trays, the surface of the soil is treated with an aqueous dispersion of the active ingredients obtained from a 25% emulsifiable concentrate. Concentrations of 4 kg of active ingredient/hectare are used. The seed trays are kept in the greenhouse at 22°-25° C. and 50-70% relative humidity and the test is evaluated after 3 weeks in accordance with the following rating.
1: plant has not germinated or has completely died
2-3: very strong action
4-6: moderate action
7-8: weak action
9: no action (as untreated control)

The compounds of Tables 1 to 6 exhibit strong herbicidal action in this test.

| Test results: pre-emergence test Application rate: 4 kg of active ingredient per hectare | | | | |
|---|---|---|---|---|
| Verb. Nr. | Avena | Setaria | Sinapis | Stellaria |
| 1.016 | 7 | 3 | 1 | 2 |
| 2.034 | 2 | 1 | 2 | 2 |
| 3.03 | 1 | 3 | 1 | 2 |

Example B2: Post-emergence herbicidal action (contact herbicide)

A number of weeds, both mono- and dicotyledonous, are sprayed post-emergence (in the 4- to 6-leaf stage) with an aqueous active ingredient dispersion at a rate of 4 kg of test compound per hectare and kept at 24°-26° C. and 45-60% relative humidity. The test is evaluated 15 days after treatment in accordance with the rating indicated in the pre-emergence test.

In this test too, the compounds of Tables 1 to 6 exhibit good herbicidal action.

| Test results: post-emergence test Application rate: 4 kg of active ingredient per hectare | | | | | | | |
|---|---|---|---|---|---|---|---|
| Verb. Nr. | Avena | Setaria | Lolium | Solanum | Sinapis | Stellaria | Phaseolus |
| 1.016 | 5 | 7 | 5 | 3 | 3 | 4 | 3 |
| 2.034 | 4 | 3 | 4 | 4 | 3 | 6 | 2 |

Example B3: Herbicidal action pre-emergence

Plastic pots are filled with expanded vermiculite (density: 0.135 g/cm$^3$, water absorption capacity: 0.565 l/l). After the non-adsorbent vermiculite has been saturated with an aqueous emulsion in deionised water containing the active ingredients in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., with illumination at approximately 20 kLux and 70% relative humidity. During the germination phase of 4 to 6 days, the pots are covered with transparent material and watered with deionised water to increase local humidity. After the 5th day, 0.5% of a commercially available liquid fertiliser (® Greenzit) is added to the water. 12 days after sowing, the test is evaluated and the effect on the test plants is assessed.

The compounds of Tables 1 to 6 exhibit a very strong herbicidal action in this test.

EXAMPLE B4: HERBICIDAL ACTION IN PADDY

The weeds *Echinochloa crus galli* and *Monocharia vaginalis*, which occur on flooded soil, are sown in plastic beakers (surface area: 60 cm$^2$; volume: 500 ml). After sowing the beakers are filled with water up to the surface of the soil. 3 days after sowing, the water level is increased to slightly above the soil surface (3-5 mm). Application is effected 3 days after sowing by spraying the beakers with an aqueous emulsion of the test compounds. The rate of application corresponds to a concentration of 4 kg of active ingredient per hectare (amount of spraying liquor=550 l/ha). The beakers containing the plants are then kept in the greenhouse under optimum growth conditions for rice weeds, i.e. at 25°-30° C. and at high humidity. The evaluation of the test takes place 3 weeks after application, the state of the plants being assessed as in the pre-emergence test. The compounds of Tables 1 to 6 damage the weeds but not the rice.

Test results: post-emergence test
Application rate: 4 kg of active ingredient per hectare

| Verb. Nr. | Echinochloa | Monochoria |
|---|---|---|
| 1.016 | 1 | 1 |
| 2.034 | 1 | 1 |
| 3.03 | 1 | 1 |

What is claimed is:

1. Imidazole derivatives of formula I

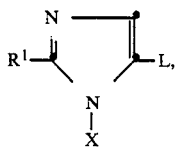

the stereochemically isomeric forms thereof, and salts thereof, in which X is a radical of the formula

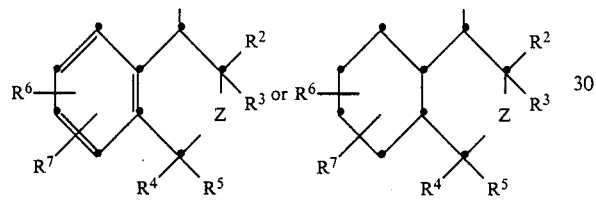

$R^1$ is hydrogen or —SH, and
L is cyano, —COOH, —COOR$^8$, —COSR$^8$, —CONR$^9$R$^{10}$, —CO—R$^{11}$, —CH$_2$—O—R$^{12}$ or a group

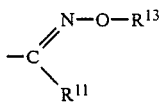

wherein
Z is oxygen, sulfur, —SO—, or —SO$_2$—
each of $R^2$ and $R^3$ independently of the other, is hydrogen, C$_1$-C$_4$alkyl, C$_2$-C$_4$alkenyl or C$_2$-C$_4$alkynyl or together they form a spirocyclically linked C$_2$-C$_6$alkylene chain,
each of $R^4$ and $R^5$, independently of the other, is hydrogen or C$_1$-C$_4$alkyl or together they form an oxo function,
$R^6$ is hydrogen, cyano, halogen, C$_1$-C$_4$alkyl, C$_1$-C$_4$haloalkyl, C$_1$-C$_4$alkoxy, C$_1$-C$_4$haloalkoxy, C$_1$-C$_4$alkylthio, C$_1$-C$_4$haloalkylthio or nitro,
$R^7$ is hydrogen, C$_1$-C$_4$alkoxy, halogen or C$_1$-C$_4$alkyl,
$R^8$ is C$_1$-C$_6$alkyl, C$_3$-C$_7$cycloalkyl, C$_2$-C$_6$alkoxyalkyl, benzyl, —CR$^{15}$R$^{16}$—C$_2$-C$_4$alkenyl or —CR$^{15}$R$^{16}$—C$_2$-C$_4$alkynyl,
$R^9$ is hydrogen, C$_1$-C$_4$alkyl, C$_1$-C$_4$alkoxy, phenyl, benzyl, —CR$^{15}$R$^{16}$—C$_2$-C$_4$alkynyl,
$R^{10}$ is hydrogen or C$_1$-C$_4$alkyl, or
$R^9$ and $R^{10}$ together with the nitrogen atom carrying them form a pyrrolidine, piperidine or morpholine radical, $R^{11}$ is C$_1$-C$_6$alkyl, C$_3$-C$_7$cycloalkyl, C$_1$-C$_4$haloalkyl, or phenyl that is unsubstituted or substituted by C$_1$-C$_4$alkyl, C$_1$-C$_4$alkoxy, nitro or by halogen,
$R^{12}$ is hydrogen, C$_1$-C$_6$alkyl, phenyl that is unsubstituted or substituted by C$_1$-C$_4$alkyl, C$_1$-C$_4$alkoxy, halogen or by nitro, C$_1$-C$_6$alkylcarbonyl, C$_1$-C$_4$haloalkylcarbonyl, or benzoyl that is unsubstituted or substituted by C$_1$-C$_4$alkoxy, halogen or by nitro,
$R^{13}$ is C$_1$-C$_4$ alkyl, —CR$^{15}$R$^{16}$—C$_2$-C$_4$ alkenyl, benzyl or —CR$^{15}$R$^{16}$—C$_2$-C$_4$ chloroalkenyl, and each of R$^{15}$ and R$^{16}$, independently of the other, is hydrogen or C$_1$-C$_4$alkyl.
each of R$^{15}$ and R$^{16}$, independently of the other, is hydrogen or C$_1$-C$_4$alkyl.

2. Compounds according to claim 1 wherein $R^1$ is hydrogen.

3. Compounds according to claim 1 wherein L is —COOR$^8$, —C—NR$^9$R$^{10}$ or —CO—R$^{11}$.

4. Compounds according to claim 3 wherein L is C$_1$-C$_4$alkoxycarbonyl.

5. Compounds according to claim 3 wherein L is —CO—NR$^9$R$^{10}$ in which each of R$^9$ and R$^{10}$, independently of the other, is hydrogen or C$_1$-C$_4$alkyl.

6. Compounds according to claim 3 wherein L is C$_1$-C$_4$alkylcarbonyl.

7. Compounds according to claim 1 wherein X is the radical

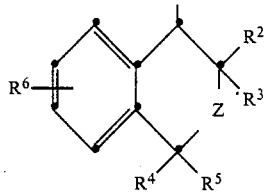

in which each of $R^2$ and $R^3$, independently of the other, is hydrogen or C$_1$-C$_4$alkyl, $R^4$ and $R^5$ are hydrogen or together form an oxo function, $R^6$ is hydrogen, C$_1$-C$_4$alkyl, C$_1$-C$_4$alkoxy or halogen, and Z is oxygen, or sulfur.

8. Compounds according to claim 1 wherein X is the radical

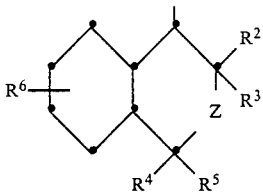

in which the ring linkage is in the trans-position, each of $R^2$ and $R^3$, independently of the other, is hydrogen or C$_1$-C$_4$alkyl, $R^4$ and $R^5$ are hydrogen, $R^6$ is hydrogen, C$_1$-C$_4$alkyl or halogen, and Z is oxygen, or sulfur.

9. Compounds according to claim 7 wherein $R^1$ is hydrogen and L is C$_1$-C$_4$-alkoxycarbonyl, C$_1$-C$_4$alkylcarbonyl, carbamoyl, methylcarbamoyl or dimethylcarbamoyl.

10. Compounds according to claim 8 wherein $R^1$ is hydrogen and L is C$_1$-C$_4$-alkoxycarbonyl, C$_1$-C$_4$alkylcarbonyl, carbamoyl, methylcarbamoyl or dimethylcarbamoyl.

11. 1-(3-methylisochroman-4-yl)-5-imidazolecarboxylic acid methyl ester according to claim 1.

12. 1-(3,3-dimethylisochroman-4-yl)-5-imidazolecarboxylic acid methyl ester according to claim 1.

13. 1-(3-methylisothiochroman-4-yl)-5-imidazolecarboxylic acid methyl ester according to claim 1.

14. 1-(3,3-dimethylisothiochroman-4-yl)-5-imidazolecarboxylic acid methyl ester according to claim 1.

15. 1-(3,3-dimethyl-1-oxoisochroman-4-yl)-5-imidazolecarboxylic acid methyl ester according to claim 1.

16. A herbicidal composition which contains an effective amount of a compound of formula I as defined in claim together with one or more carriers and/or adjuvants.

17. A method of controlling undesired plant growth, which method comprises treating the plants or the locus thereof with a herbicidally effective amount of a compound of formula I as defined in claim 1.

18. A method for selectively controlling weeds in crops of useful plants, which method comprises applying to the crops of useful plants a compound of formula I as defined in claim 1 in an amount that is herbicidally effective against the weeds.

19. A method according to claim 18 wherein the crops of useful plants are maize, rice or cereal crops.

20. A method according to claim 18 wherein the useful plant crop is rice.

* * * * *